(12) United States Patent
Soma

(10) Patent No.: US 8,147,045 B2
(45) Date of Patent: Apr. 3, 2012

(54) LIQUID APPLICATOR AND LIQUID SUPPLY METHOD TO BE USED IN LIQUID APPLICATOR

(75) Inventor: Tsunenori Soma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 114 days.

(21) Appl. No.: 12/499,058

(22) Filed: Jul. 7, 2009

(65) Prior Publication Data

US 2009/0273627 A1 Nov. 5, 2009

Related U.S. Application Data

(62) Division of application No. 10/772,361, filed on Feb. 6, 2004, now Pat. No. 7,568,779.

(30) Foreign Application Priority Data

Feb. 10, 2003 (JP) ................................. 2003-032433

(51) Int. Cl.
*B41J 2/175* (2006.01)
(52) U.S. Cl. ........................................................ 347/85
(58) Field of Classification Search ............... 347/85, 347/86, 87
See application file for complete search history.

(56) References Cited

U.S. PATENT DOCUMENTS

| | | | | |
|---|---|---|---|---|
| 4,313,124 A | 1/1982 | Hara | ........................ | 346/140 R |
| 4,345,262 A | 8/1982 | Shirato et al. | ............. | 346/140 R |
| 4,459,600 A | 7/1984 | Sato et al. | ................. | 346/140 R |
| 4,463,359 A | 7/1984 | Ayata et al. | ..................... | 346/1.1 |
| 4,558,333 A | 12/1985 | Sugitani et al. | ........... | 346/140 R |
| 4,723,129 A | 2/1988 | Endo et al. | ...................... | 346/1.1 |
| 4,740,796 A | 4/1988 | Endo et al. | ...................... | 346/1.1 |
| 4,831,389 A * | 5/1989 | Chan | ............................... | 347/86 |
| 5,369,429 A * | 11/1994 | Erickson | ............................ | 347/7 |
| 5,958,342 A | 9/1999 | Gamble et al. | ............ | 422/140 R |
| 6,039,430 A | 3/2000 | Helterline et al. | .............. | 347/19 |
| 6,053,597 A | 4/2000 | Hirota | .............................. | 347/19 |
| 6,123,863 A | 9/2000 | Shimomura et al. | ........... | 216/27 |
| 6,264,322 B1 * | 7/2001 | Axtell et al. | .................. | 347/108 |
| 6,585,345 B2 | 7/2003 | Kosugi | ............................. | 347/19 |
| 6,655,775 B1 | 12/2003 | Raman et al. | ................... | 347/19 |
| 6,938,976 B2 | 9/2005 | Siwinski et al. | ................ | 347/19 |
| 7,059,699 B2 | 6/2006 | Asauchi et al. | ................. | 347/10 |
| 2002/0143475 A1 | 10/2002 | Okamura et al. | ................ | 702/31 |
| 2002/0153435 A1 | 10/2002 | Udagawa et al. | ............ | 239/548 |
| 2002/0182610 A1 | 12/2002 | Okamoto et al. | ................ | 435/6 |

FOREIGN PATENT DOCUMENTS

| | | |
|---|---|---|
| FR | 2579856 | 10/1986 |
| JP | 59-123670 | 7/1984 |
| JP | 59-138461 | 8/1984 |
| JP | 2000-513266 | 10/2000 |
| JP | 2001-296303 | 10/2001 |

(Continued)

*Primary Examiner* — Anh T. N. Vo
(74) *Attorney, Agent, or Firm* — Fitzpatrick, Cella, Harper & Scinto

(57) ABSTRACT

A liquid applicator suitable for manufacturing probe arrays comprises a liquid ejection section having a plurality of sets of a liquid ejecting nozzle adapted to eject liquid onto a medium, a liquid containing section communicating with the liquid ejecting nozzle and a supply port for supplying liquid to the liquid containing section, a liquid supply section having a liquid supply member arranged therein to store liquid to be applied and adapted to supply liquid to the liquid ejection section by way of the supply ports, an information recording body arranged at the liquid ejection section and/or the liquid supply member of the liquid supply section and an information reading device adapted to read information recorded in the information recording body.

6 Claims, 21 Drawing Sheets

FOREIGN PATENT DOCUMENTS

| | | |
|---|---|---|
| JP | 2002-286735 | 10/2002 |
| JP | 2002-296287 | 10/2002 |
| JP | 2002-318232 | 10/2002 |

\* cited by examiner

FIG. 5

| SYMBOL OF LIQUID RECEIVING PARTY | ID NUMBER | TIME LIMIT OF USE | NUMBER OF COLUMNS | NUMBER OF ROWS |
|---|---|---|---|---|
| J | 00001 | 20021231 | 16 | 16 |

FIG. 6

| SYMBOL OF LIQUID SUPPLYING PARTY | ID NUMBER | TIME LIMIT OF USE | AUTHORIZED MAXIMUM NUMBER OF TIMES OF SUPPLY | NUMBER OF COLUMNS | NUMBER OF ROWS | REGION NO. IN LIQUID RECEIVING CONTAINER |
|---|---|---|---|---|---|---|
| K | 00001 | 20020131 | 10 | 08 | 04 | 01 |

FIG. 7

| WELL PLATE ID NO | NUMBER OF TIMES OF SUPPLY |
|---|---|
| 00001 | 2 |
| 00002 | 2 |
| 00003 | 1 |
| ⋮ | |

FIG. 8

| REGION NO. IN LIQUID RECEIVING CONTAINER | POSITION ID NO. OF WELL PLATE DEPOT STORING CORRESPONDING WELL PLATE |
|---|---|
| 1 | ⑤ |
| 2 | ③ |
| 3 | ⑧ |
| 4 | ④ |
| 5 | ① |
| 6 | ⑦ |
| 7 | ② |
| 8 | ⑥ |

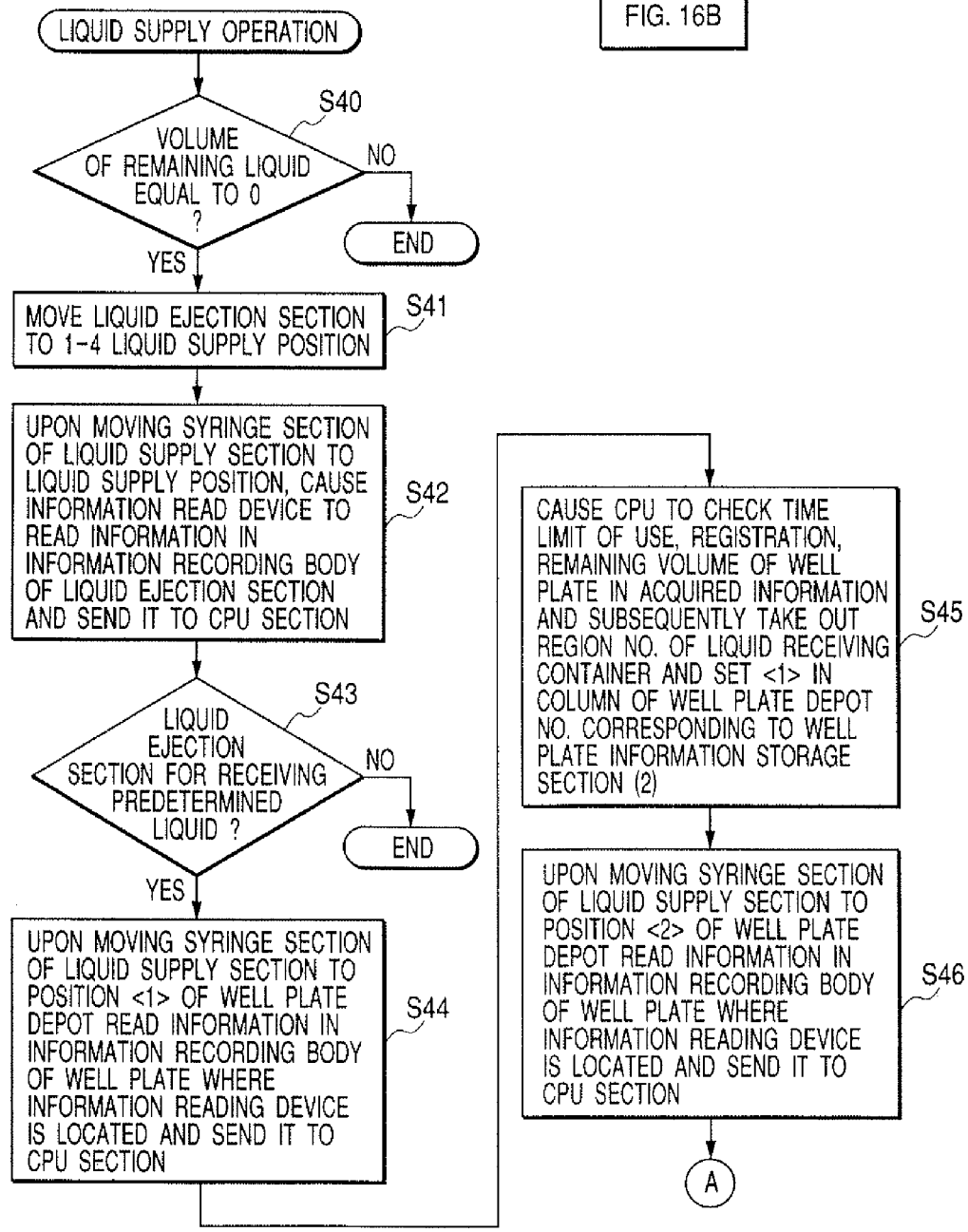

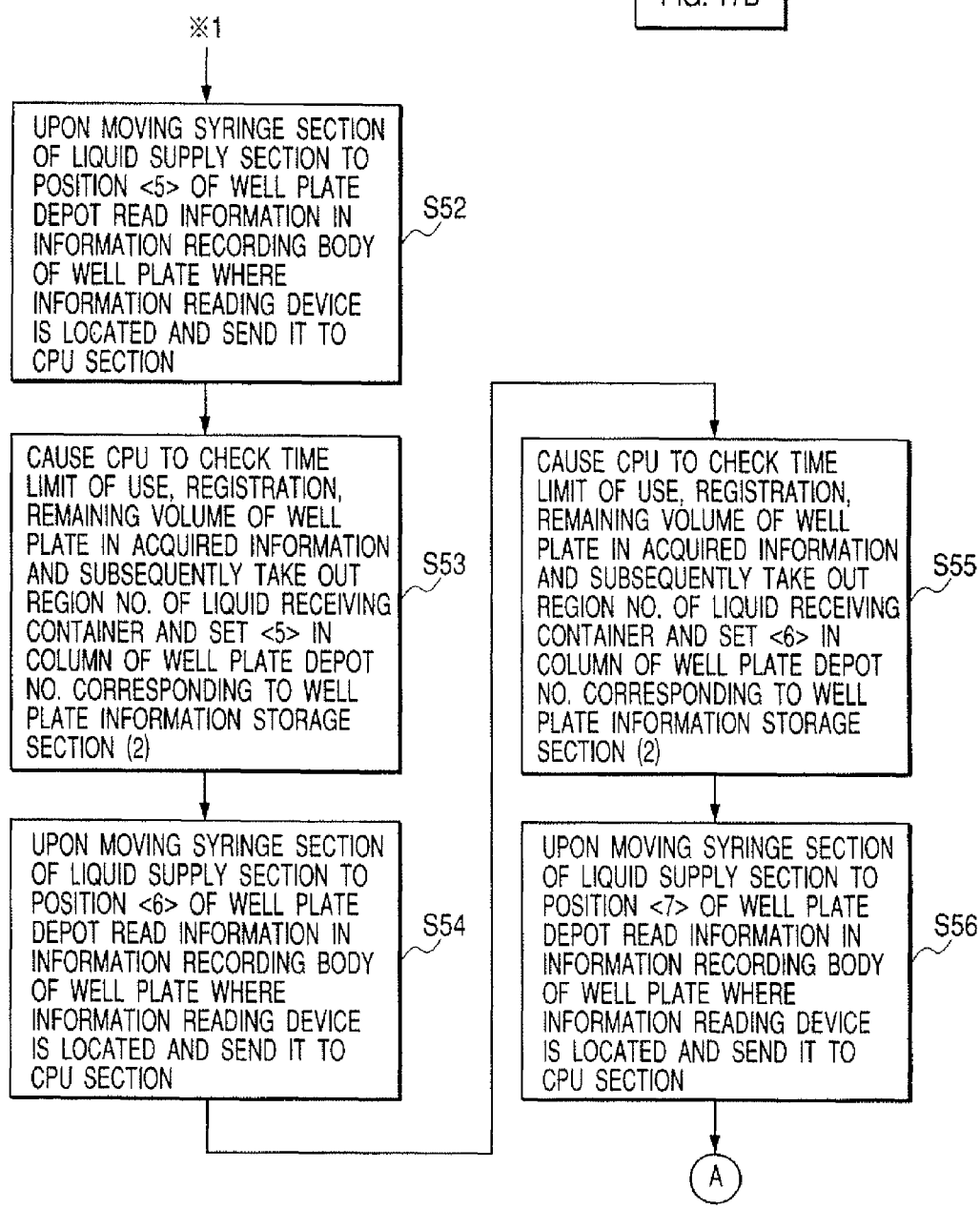

LIQUID APPLICATOR AND LIQUID SUPPLY METHOD TO BE USED IN LIQUID APPLICATOR

This application is a division of application Ser. No. 10/772,361, filed Feb. 6, 2004 (allowed), the contents of which are incorporated herein by reference.

BACKGROUND OF THE INVENTION

1. Field of the Invention

This invention relates to a liquid applicator and a liquid supply method to be used in a liquid applicator.

2. Related Background Art

Probes that can uniquely be bonded to a target substance having a specific base sequence such as a short fragment of single-strand DNA and are labeled with a radio isotope or a fluorescent substance are being utilized for gene diagnosis and analysis of the base sequence of a genetic DNA. Like ink, liquid containing such probes can be ejected by means of a printing technology such as ink-jet printing technology.

As means for providing a plurality of different probes simultaneously, probe carriers such as DNA chips on which a probe array is formed by arranging, on a medium such as glass substrate, a multiple of probes that can be bonded to different target substances to be detected are attracting attention.

In recent years, research efforts have been paid to apply techniques relating to ink-jet printers to the manufacture of probe carriers. Currently, it is possible to make a single probe carrier to securely hold tens of thousands of different probes. An ink-jet printer can eject a very small ink droplet from a nozzle and precisely and securely deposit it at a target position on a recording medium. Thus, a high density probe carrier can be manufactured at a time by applying various kinds of probe-containing liquid in place of ink.

A method comprising a series of steps for manufacturing a probe array by supplying probe-containing liquid from a well plate to the reservoir of a liquid ejector, which operates as liquid applicator, and ejecting probe-containing liquid from the liquid ejector has been devised. It is assumed for this technique that a certain number of arrays are manufactured continuously. This technique is described in Japanese Patent Application Laid-Open No. 2000-513266 and U.S. Pat. No. 5,958,342.

Japanese Patent Application Laid-Open No. 2002-318232 discloses a method of efficiently manufacturing probe arrays, using a liquid ejector comprising a number of sets of a liquid reservoir that stores probe-containing liquid and a liquid ejecting nozzle that communicates with the liquid reservoir, as corresponding at least to the number of probes.

Japanese Patent Application Laid-Open No. 2002-296287 describes an applicator to be used with tanks that store probe-containing liquid and to which respective bar code seals are applied in order to control the liquid in the inside by using the bar codes so that the tanks can be arranged reliably as corresponding to the array.

SUMMARY OF THE INVENTION

The present invention provides a liquid applicator having a liquid ejection section suitable for manufacturing probe arrays and a method of efficiently supplying liquid to the liquid ejection section.

More specifically, in an aspect, the present invention provides a method of supplying liquid to be applied by a liquid applicator having a liquid ejection section, from a liquid supply member arranged in a liquid supply section to the liquid ejection section, the liquid ejection section having a plurality of sets of a liquid ejecting nozzle, a liquid containing section communicating with the liquid ejecting nozzle and a supply port for supplying liquid to the liquid containing section, the liquid supply member and/or the liquid ejection section being provided with an information recording body storing information, the method comprising:

reading the information; and supplying liquid to be applied from the liquid supply member to the liquid containing sections by way of the supply ports according to the information.

In another aspect of the invention, there is provided a liquid applicator comprising: a liquid ejection section adapted to eject liquid onto a medium; a liquid supply section having a liquid supply member arranged therein to store liquid to be applied and adapted to supply liquid to the liquid ejection section; an information recording body arranged at the liquid ejection section and/or the liquid supply member of the liquid supply section; and an information reading device adapted to read information recorded in the information recording body.

The liquid ejection section has a plurality of sets of a liquid ejecting nozzle, a liquid containing section communicating with the liquid ejecting nozzle and a supply port for supplying liquid to the liquid containing section. Preferably, the liquid supply section has a plurality of syringes arranged so as to correspond to the arrangement of the supply ports in order to simultaneously supply liquid to the plurality of supply ports.

The liquid ejection section and/or the liquid supply member is provided with an information recording body, which stores information specific to it, so that liquid may be supplied accurately and reliably to the liquid ejection section.

In a liquid applicator according to the invention, liquid is automatically supplied to the plurality of liquid containing sections of the liquid ejection section. Therefore, the rate at which probe arrays can be manufactured successively is not affected by the amount of liquid stored in the liquid containing sections of the liquid ejection section so that the process of manufacturing probe arrays can be continued for a long period of time. Additionally, since an information recording body is attached to the liquid ejection section and/or the liquid supply member of the liquid supply section, not only information specific to the type of liquid to be used by the liquid applicator but also information on the amount of liquid remaining in the liquid ejection section, the expiration date of the guaranteed quality of liquid, etc., can be stored in the information recording body so that the liquid ejection section and the liquid supply section can be controlled individually.

Still additionally, liquid wells of the liquid supply section and supply ports of the liquid ejection section are arranged to show a matched relationship so that liquid may be supplied simultaneously to the plurality of supply ports. Moreover, the pitch of arrangement of the liquid wells of the liquid supply section is made equal to integer times of the pitch of arrangement of the supply ports of the liquid ejection section so that liquid can be supplied smoothly to the liquid ejection section whose supply ports are arranged at a small pitch and hence arrays can be printed continuously at a high rate to improve the throughput of array manufacturing.

For the purpose of the present invention, preferably, the liquid ejection section includes an information recording body that contains at least information indicating that the liquid ejection section is the liquid receiving side along with a plurality of liquid receiving containers and a plurality of nozzles.

Preferably, the liquid supply member comprises a plurality of well plates, each carrying a plurality of liquid wells formed therein, which can store different types of liquid. Each of the well plates is provided with an information recording body that stores information indicating that it is the liquid supplying side, information identifying the well plate and information indicating the region of the corresponding liquid container in the liquid ejection section to which liquid is to be supplied from it. The information in the information recording body is expressed in a read device readable form such as bar codes and two-dimensional codes.

Preferably, the liquid supply section includes a syringe section having a plurality of syringes and a plurality of drive sections, a tip replacing section for replacing the tips at the front ends of the syringes when the liquid to be used is replaced and well plate depots where respective well plates are arranged.

For example, when liquid to be applied to a medium by the liquid applicator is supplied to the liquid receiving containers, firstly the liquid applicator reads the information stored in the information recording bodies attached respectively to the liquid ejection section and the plurality of well plates and confirms that the liquid ejection section and the plurality of well plates will operate properly before it starts supplying liquid. More specifically, the liquid applicator checks the time limit of the use of the liquid contained in each of the well plates and, if the well plates have been used before, the amount of liquid remaining in each of the well plates to confirm that the liquid ejection section and the plurality of well plates will operate properly. To be more accurately, the applicator checks the amount of liquid remaining in each of the well plates by seeing the number of times for which liquid has been supplied from the well plate to the corresponding liquid receiving container that is stored in the corresponding information recording body. When the liquid applicator operates to supply liquid, it determines the region of each of the liquid receiving containers to which liquid is supplied from the corresponding well plate according to the information read from the corresponding information recording body.

BRIEF DESCRIPTION OF THE DRAWINGS

FIG. 5 is a schematic illustration of the information stored in information recording body 13 of the liquid ejection section 1;

FIG. 6 is a schematic illustration of the information stored in the information recording bodies 31 through 38 of the well plates;

FIG. 7 is a schematic illustration of the information stored in the well plate information storage section (1) 7;

FIG. 8 is a schematic illustration of the information stored in the well plate information storage section (2) 8;

DESCRIPTION OF THE PREFERRED EMBODIMENTS

Now, the present invention will be described by referring to the accompanying drawings that illustrate preferred embodiments of the invention.

Figure 1:
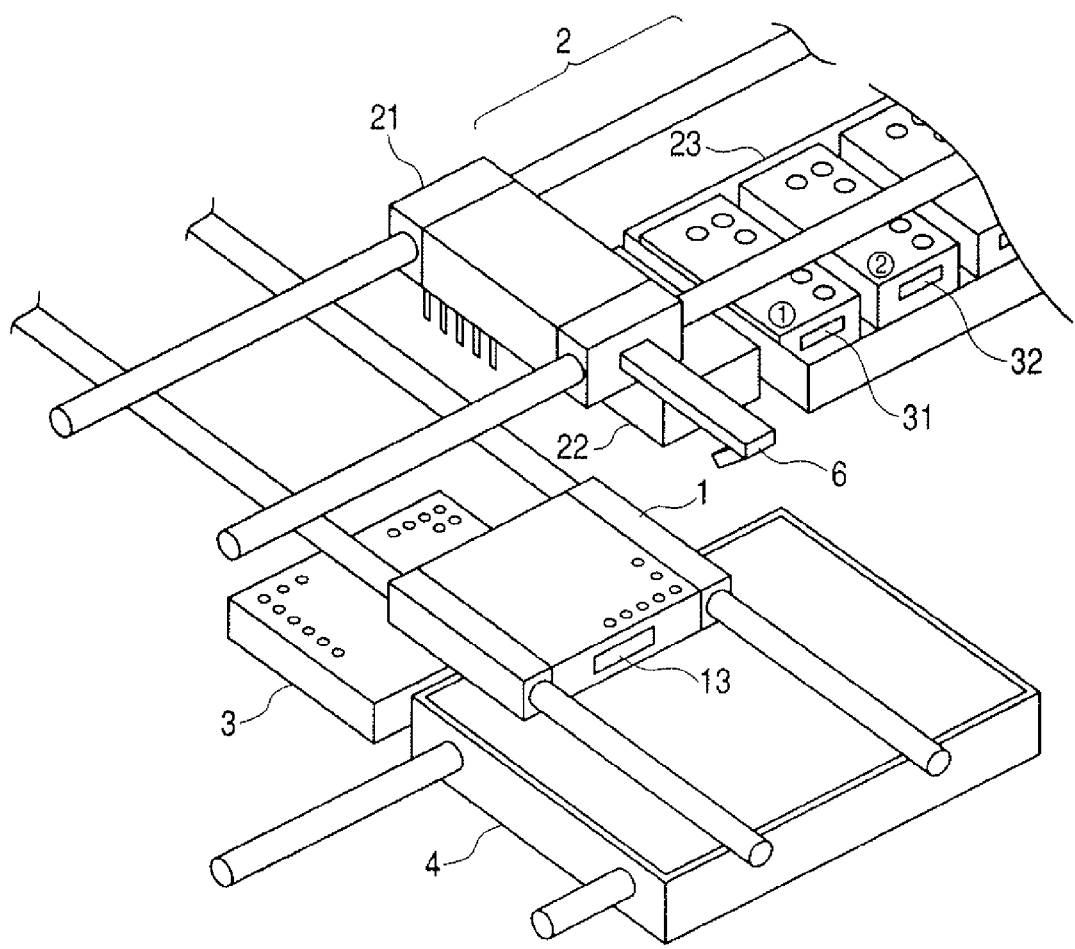
FIG. 1 is a schematic perspective view of an embodiment of liquid applicator according to the invention, showing how it appears.

Referring firstly to FIG. 1, an embodiment of liquid applicator according to the invention and adapted to apply liquid to a medium comprises a liquid ejection section 1, a liquid supply section 2, a cleaning section 3, a medium conveying section 4 and an information reading device 6.

The liquid ejection section 1 is adapted to move along a guide rail by means of a drive section contained in it. It can move back and forth repeatedly above the medium conveying section 4 while the liquid applicator is operating to apply liquid to a medium. It can move to a position where it receives liquid supplied by the liquid supply section 2 and also to a position where it is cleaned by the cleaning section 3. An information recording body 13 is attached to the liquid ejection section 1.

The liquid supply section 2 includes a syringe section 21, a tip replacing section 22 and a well plate depot 23 for receiving a plurality of well plates. The syringe section 21 of the liquid supply section 2 has a multiple of syringes and can suck and eject various different types of liquid at a time by means of a drive section contained in it. A cylindrical tip is attached to the front end of each syringe in order to hold liquid there. The tip can be taken off by the tip replacing section 22 so that a replacement tip may be attached to the front end of the syringe. A number of well plates, each having a multiple of wells, are arranged in the well plate depot 23.

The syringe section 21 is adapted to move above the tip replacing section 22 and the well plate depot 23 along a guide rail. To replace any of the tips, it stops at the tip replacing section 22 and replaces the tip(s) by means of the drive section contained in it. To supply liquid, it stops at the position of a selected well plate and sucks liquid from the well plate by means of the drive section. The guide rail of the liquid supply section 2 crosses the guide rail of the liquid ejection section 1 at a position above the latter guide rail. The syringe section 21 can move to the crossing, where it ejects liquid to give it to the liquid ejection section 1. Information recording bodies 31, 32, . . . are attached to the respective well plates. A means for controlling the environment (temperature, moisture rate, etc.) of the well plate depot may be provided.

The cleaning section 3 is located below the guide rail of the liquid ejection section 1. For a cleaning operation, it rises as a whole by means of a drive section contained in it until it contacts the lower surface of the liquid ejection section 1. Subsequently, it can suck out the liquid remaining in the liquid ejection section 1 by means of a pump contained in it.

The medium conveying section 4 can move in a direction perpendicular to the moving direction of the liquid ejection section 1, holding a medium. Thus, liquid can be ejected to the entire surface of the medium by combining the movement of the medium conveying section 4 and that of the liquid ejection section 1.

The medium is attached to and removed from the medium conveying section 4 by a conveyance mechanism (not shown).

The information reading device 6 is fitted to the syringe section 21 of the liquid supply section 2. It reads the information stored in the information recording body 13 attached to the liquid ejection section 1 when the syringe section 21 is located above the liquid ejection section 1. It reads the information stored in the information recording bodies 31, 32, . . . attached to the respective well plates when the syringe section 21 is located above the well plates in the well plate depot 23.

This embodiment of liquid applicator is adapted to detect the amount of liquid consumed from the reservoir of the liquid ejection section 1 and, if the amount of the remaining liquid falls below a predetermined level, liquid is automatically supplied from the well plates to the reservoir so that the liquid applicator may keep on manufacturing arrays for a long period of time. It is so arranged that a number of different types of liquid can be collectively supplied from the well plates to the reservoir of the liquid ejection section in order to simplify the operation of handling probe-containing liquid when supplying the latter.

Different types of liquid can be simultaneously supplied with ease from the well plates to the liquid ejection section when the spaces separating the syringes are so designed as to correspond to those separating the well plates and those separating the supply ports of the liquid ejection section. For instance, liquid can be supplied to all the target supply ports at a time in a single supply operation when the syringes, the wells and the supply ports are arranged at a same pitch (and hence spaced uniformly). Liquid can be supplied to every other supply ports at a time in a single supply operation when the well plates and the syringes are arranged at a same pitch and the pitch of arrangement of the supply ports is a half of that of the well plates and the syringes. Thus, the number of operations required for supplying liquid can be remarkably reduced.

It is advantageous to print arrays highly densely from the viewpoint of improving the efficiency of using them for biochemical reactions sometime thereafter. Arrays can be printed at an enhanced rate when the nozzles of the liquid ejection section are arranged at a small pitch. Therefore, it is desirable to arrange the nozzles of the liquid ejection section at a small pitch. On the other hand, it is difficult to arrange syringes at a small pitch in the liquid supply section because of the provision of the syringe mechanism for sucking and delivering liquid.

Thus, from the viewpoint of densely arranging the nozzles of the liquid ejection section, it is preferable to make the pitch of arrangement of the syringes of the liquid supply section is equal to integer times of the pitch of arrangement of the nozzles of the liquid ejection section. If, for example, the pitch of arrangement of the nozzles of the liquid ejection section is a half of that of the syringes of the liquid supply section, liquid is supplied to every other liquid containing section of the liquid ejection section. Then, subsequently, liquid is supplied to the remaining every other liquid containing section of the liquid ejection section after shifting the syringes by the pitch of arrangement of the nozzles of the liquid ejection section.

For the purpose of the present invention, bar codes may be used on the information recording bodies 31, 32, . . . and the information in the form of bar codes of each information recording body includes the ID of the well plate, the capacity of the well plate and the expiration date of effectiveness of liquid. Thus, it is possible to elaborately and individually confirm different types of liquid when liquid is brought to the liquid ejection section.

Additionally, an information recording body 13 carrying bar codes may be attached to the liquid ejection section so that the implementation of the liquid ejection section may be visually confirmed.

While the bar codes of each of the information recording bodies are made to carrying information including the ID of the well plate, the capacity of the well plate and the expiration date of effectiveness of liquid and the applicator is adapted to operate, using theses pieces of information whenever necessary, in the above description, it may alternatively be so arranged that the information recording body carry only the bar code of the ID of the corresponding well plate and all the remaining information is stored in the applicator itself so that the latter operates, using the information stored in itself.

Since the applicator operates after the information reading device reads information from the information recording bodies, liquid can be supplied from a plurality of well plates that are arranged randomly to any desired region(s) of the liquid ejection section.

When the effective date of any of the well plates has been expired or when the capacity has been reduced due to repeated use, the operation of the liquid applicator may be suspended instantaneously to replace the well plate(s) so that the efficiency and reliability of operation of the liquid applicator will be remarkably improved.

Preferably, arrays manufactured by means of a liquid applicator according to the invention are such that probes contained therein may be anchored to the medium. The term "a probe" as used herein refers to one that can be uniquely bonded to a specific target substance.

Probes may include oligonucleotide, polynucleotide and other polymers that can recognize a specific target. The term "probes" as used herein refers to individual molecules having a probe feature such as polynucleotide molecules or a group of molecules such as a group of polynucleotide molecules that are surface-fixed to dispersed positions and have a same molecular arrangement. Probes may include molecules that are called ligands. A probe and a target are frequently interchangeably used. It can be bonded to or can become to be bonded to a target as part of a ligand-antiligand (also referred to as receptor) pair. For the purpose of the invention, probes and targets may include bases and similar substances that are found in the nature.

Now, an example of liquid supply method according to the invention will be described by referring to flow charts.

Figure 2:
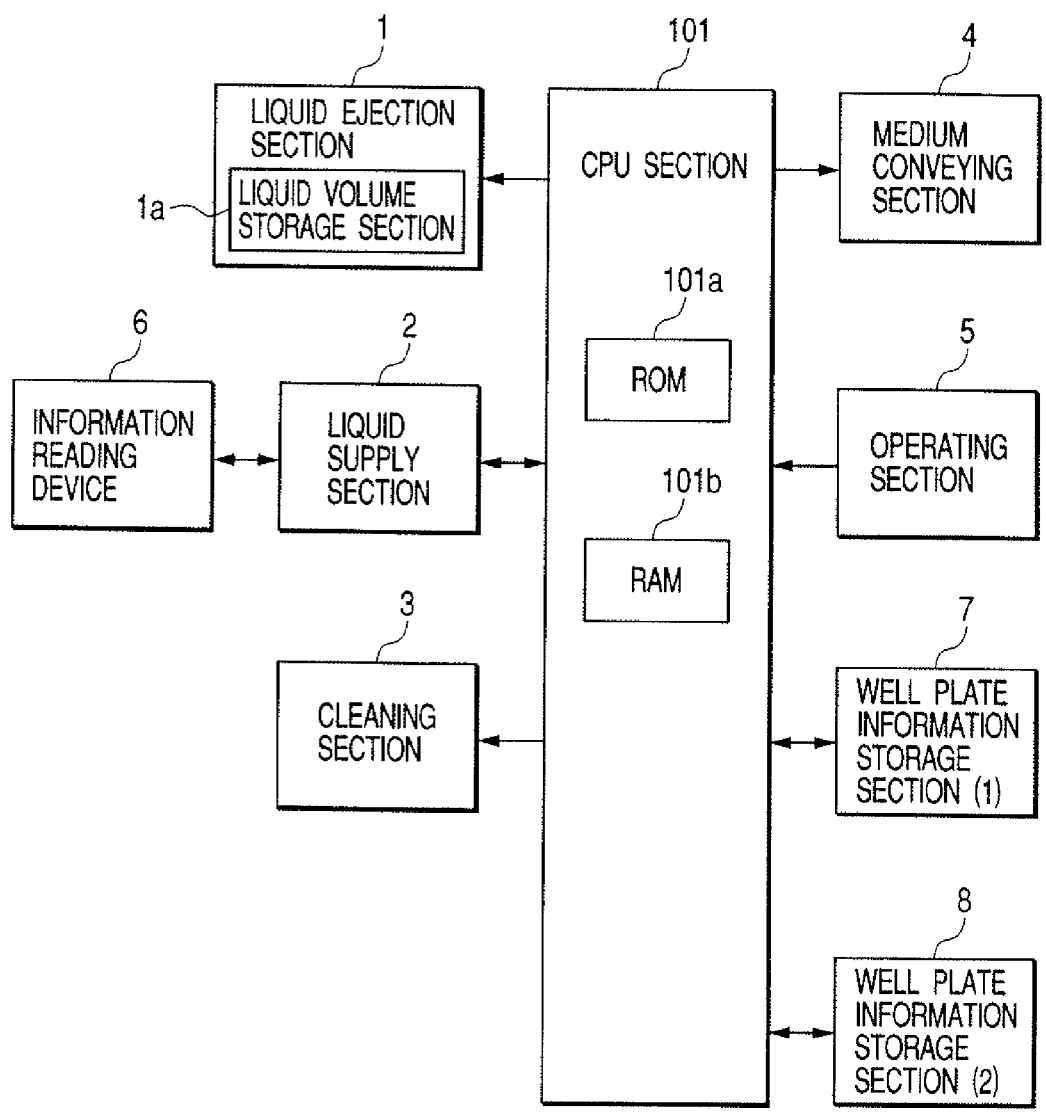
FIG. 2 is a functional block diagram of the embodiment of liquid applicator of FIG. 1.

FIG. 2 is a functional block diagram of a liquid applicator according to the invention. Referring to FIG. 2, a CPU section 101 includes a ROM 101a where programs are stored and a RAM 101b that can be used to read and retrieve programs and data. The CPU section 101 issues instructions to the component sections for operation and receives information on the outcome of the performed operation. An operating section 5 is provided with a group of keys to be used by the operator to enter commands. As the key group is operated, a command for starting a liquid applying operation may be issued to the CPU section 101. A well plate information storage section (1) 7 is a non-volatile memory device for storing the ID number of the well plate and the number of times of liquid supply as read by the information reading device in order to store the history of all the well plates. A well plate information storage section (2) 8 stores the relationship between each of the well plates in the well depot 23 and the corresponding liquid supply region of the liquid ejection section 1, which will be described hereinafter.

A liquid volume storage section 1a is also a non-volatile memory device that is located in the liquid ejection section 1 and adapted to store the volume of each of the liquid receiving containers as will be described hereinafter. After a cleaning operation, the CPU section 101 operates to write 0 in the liquid volume storage section 1a. After a liquid supplying operation, the CPU section 101 operates to write the value of the volume of liquid supplied in the liquid volume storage section 1a.

After a liquid applying operation, the CPU section 101 operates to read the numerical data on the volume of liquid from the liquid volume storage section 1a and decrements the numerical data by a value corresponding to the volume of the applied liquid. The revised numerical value is then written into the liquid volume storage section 1a.

The CPU section 101 operates to determine the volume of the applied liquid by adding up the numbers of times of liquid ejection from the nozzles and multiplying the sum of the addition by the amount by which liquid is assumed to be ejected in a single liquid ejection.

Figure 3:
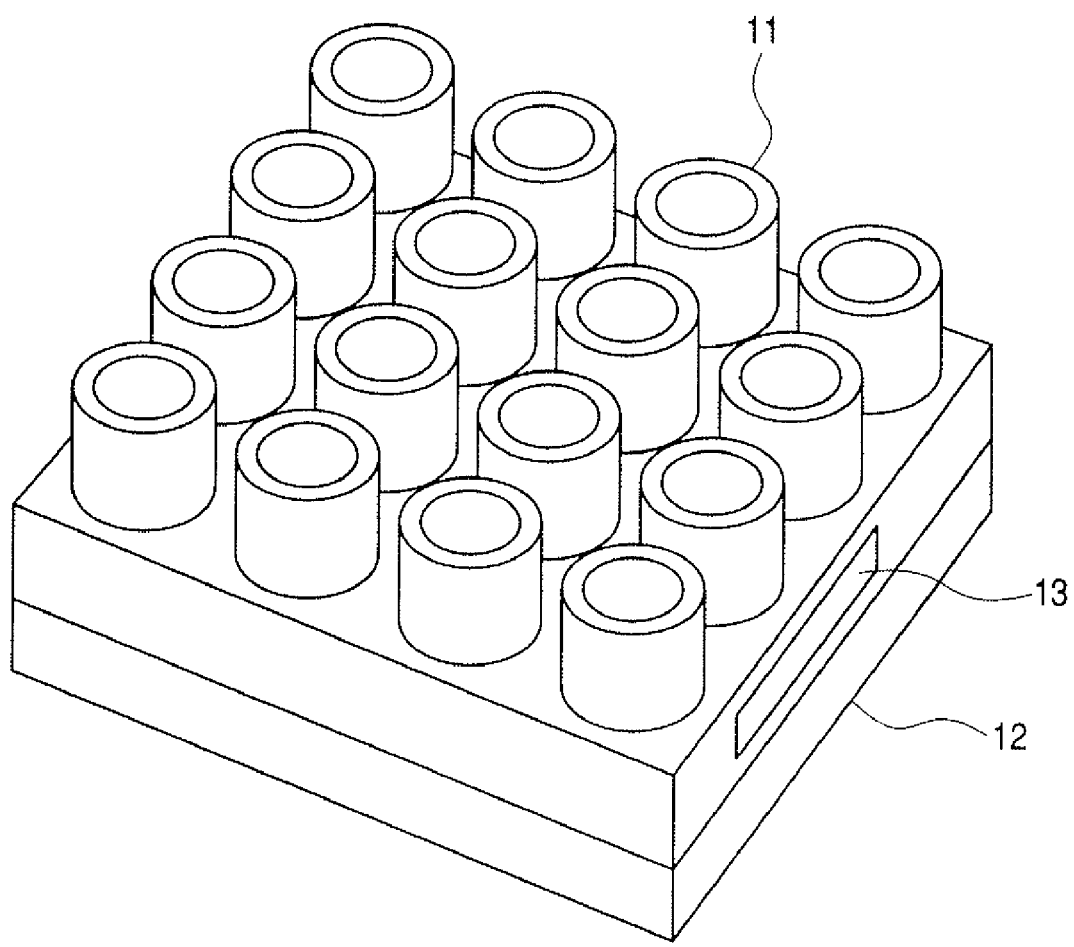
FIG. 3 is a schematic perspective view of a principal part of the liquid ejection section 1.

FIG. 3 is a schematic perspective view of a principal part of the liquid ejection section 1. It may be so designed that the principal part is removably fitted to the liquid ejection section 1. A number of liquid receiving containers 11 that are open upwardly are arranged on the top surface of the principal part. The openings of the liquid receiving containers 11 are supply ports that are directed in a same direction so that liquid may be supplied simultaneously from a number of syringes.

A nozzle section 12 (not shown) is arranged at the underside, where nozzles are formed so as to communicate with the respective liquid receiving containers 11. Each nozzle has a drive circuit that operates to eject liquid to the outside. Thus, each nozzle ejects liquid according to an instruction from the CPU section 101. In this embodiment, liquid receiving containers 11 are arranged at a constant pitch in the liquid ejection section 1 to form 16 rows and 16 columns.

However, it will be appreciated that the configuration of the liquid ejection section of a liquid applicator according to the invention is by no means limited to the above definition and the configuration described in Japanese Patent Application Laid-Open No. 2002-318232 may alternatively be used for the purpose of the present invention.

Figure 4:
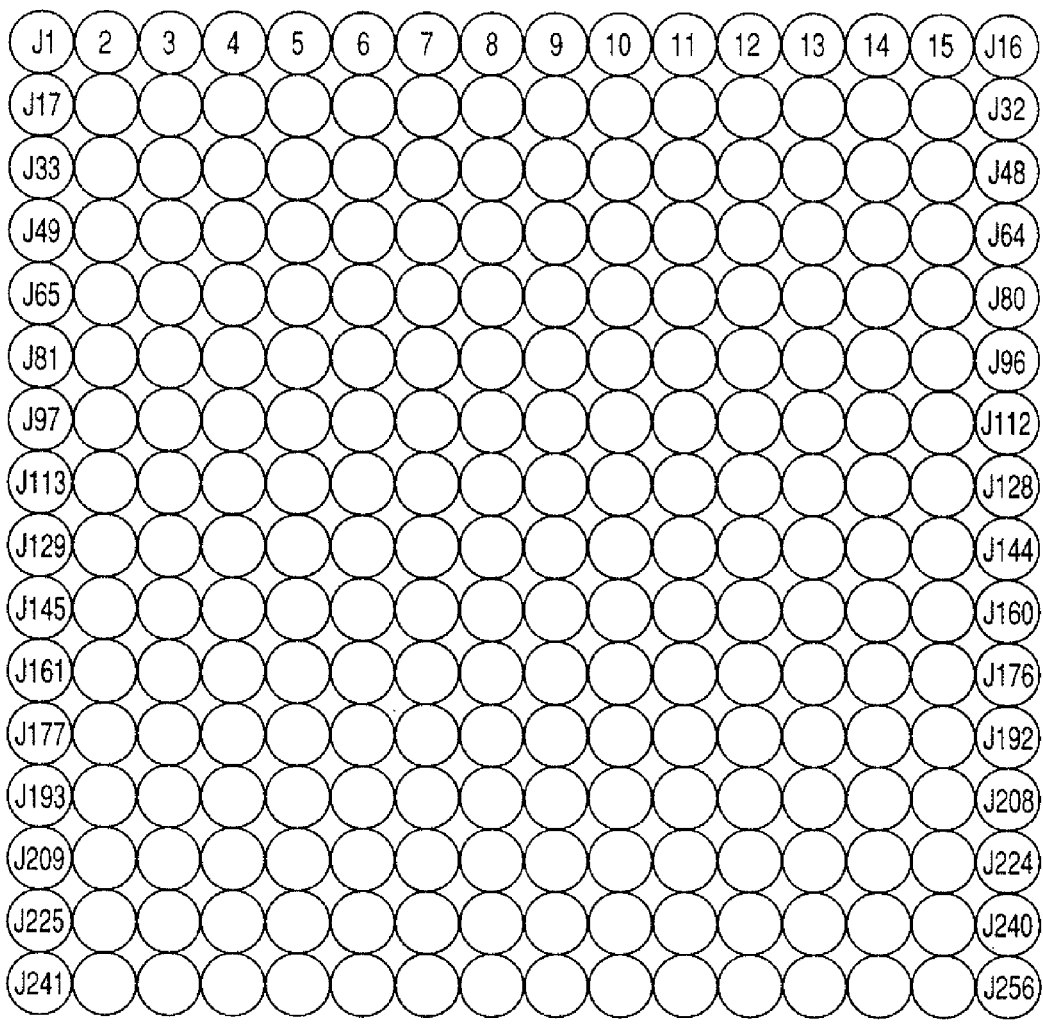
FIG. 4 is a schematic illustration of the addressed liquid receiving containers 11 of the liquid ejection section 1, the addresses being used as positional information of the liquid containers 11.
Figure 9:
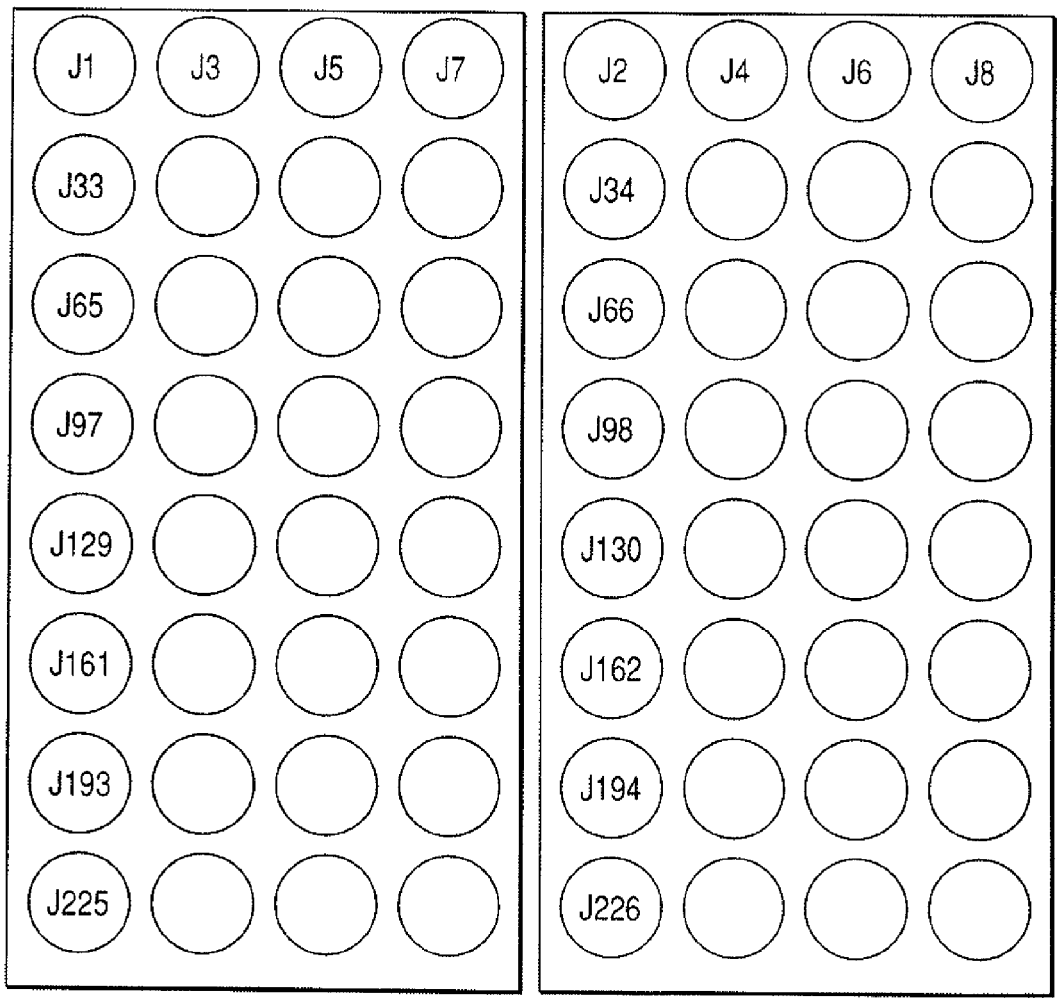
FIG. 9 is a schematic illustration of the correspondence of the addresses that are used as positional information of the liquid receiving containers 11 of the liquid ejection section 1 and the wells of each of the well plates.
Figure 10:
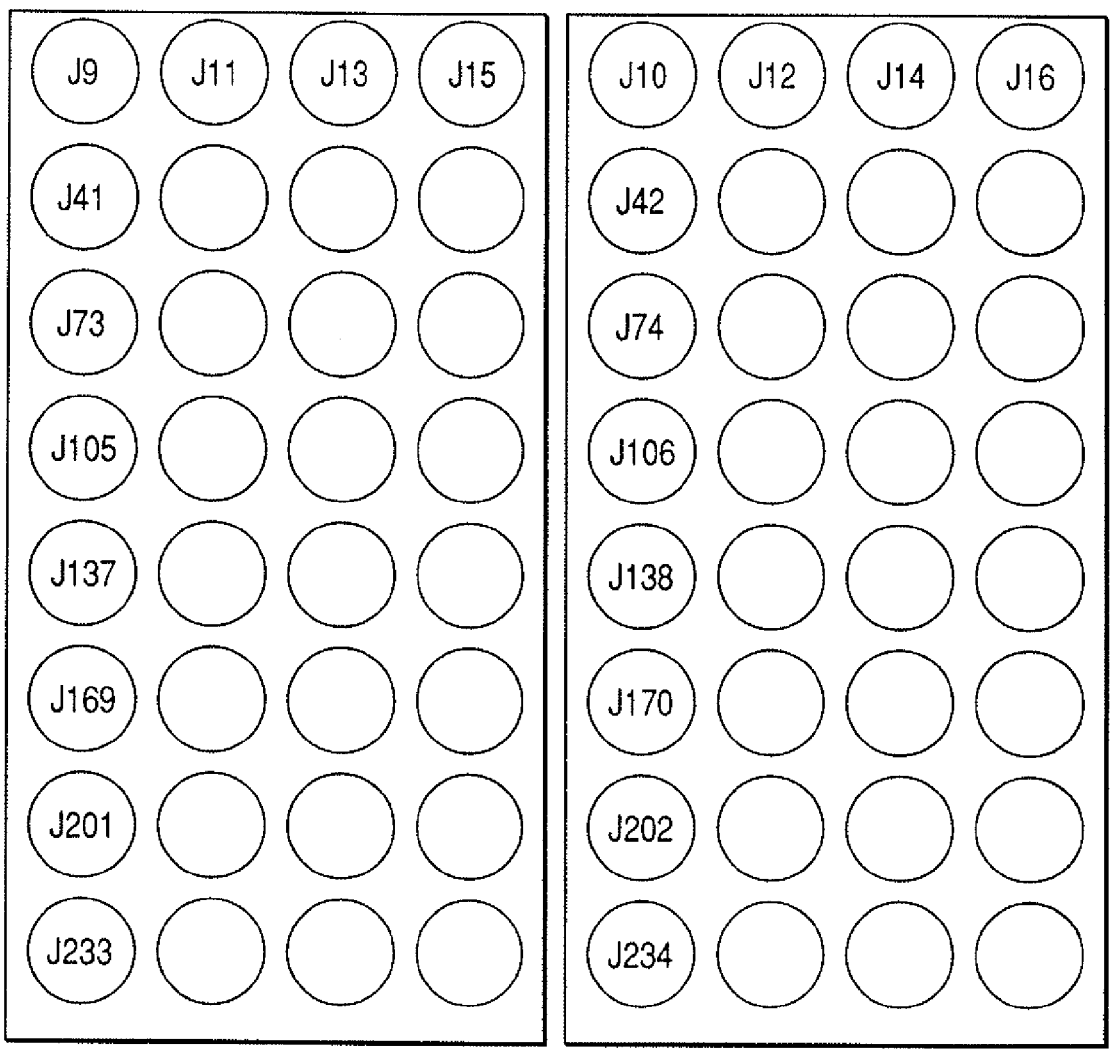
FIG. 10 is a schematic illustration of the correspondence of the addresses that are used as positional information of the liquid receiving containers 11 of the liquid ejection section 1 and the wells of each of the well plates (as continued from FIG. 9)
Figure 11:
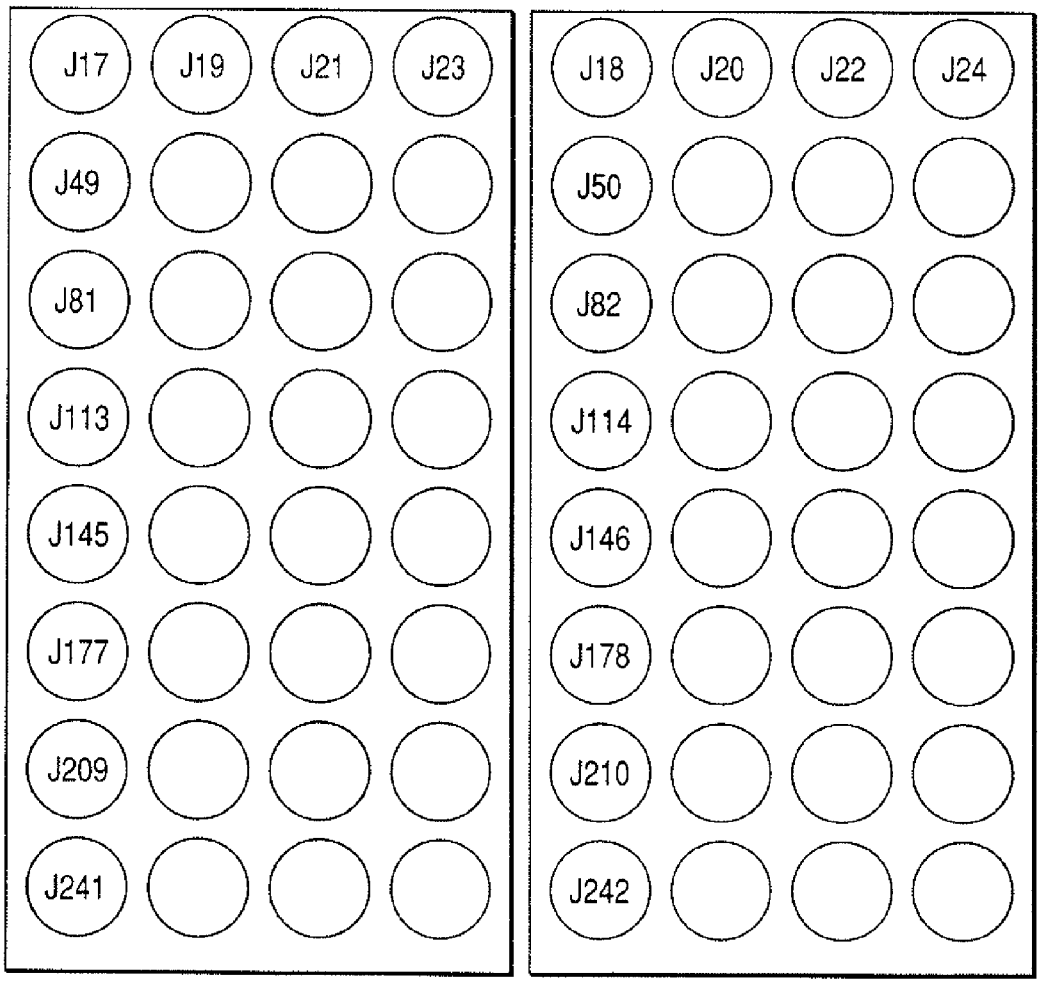
FIG. 11 is a schematic illustration of the correspondence of the addresses that are used as positional information of the liquid receiving containers 11 of the liquid ejection section 1 and the wells of each of the well plates (as continued from FIG. 10)
Figure 12:
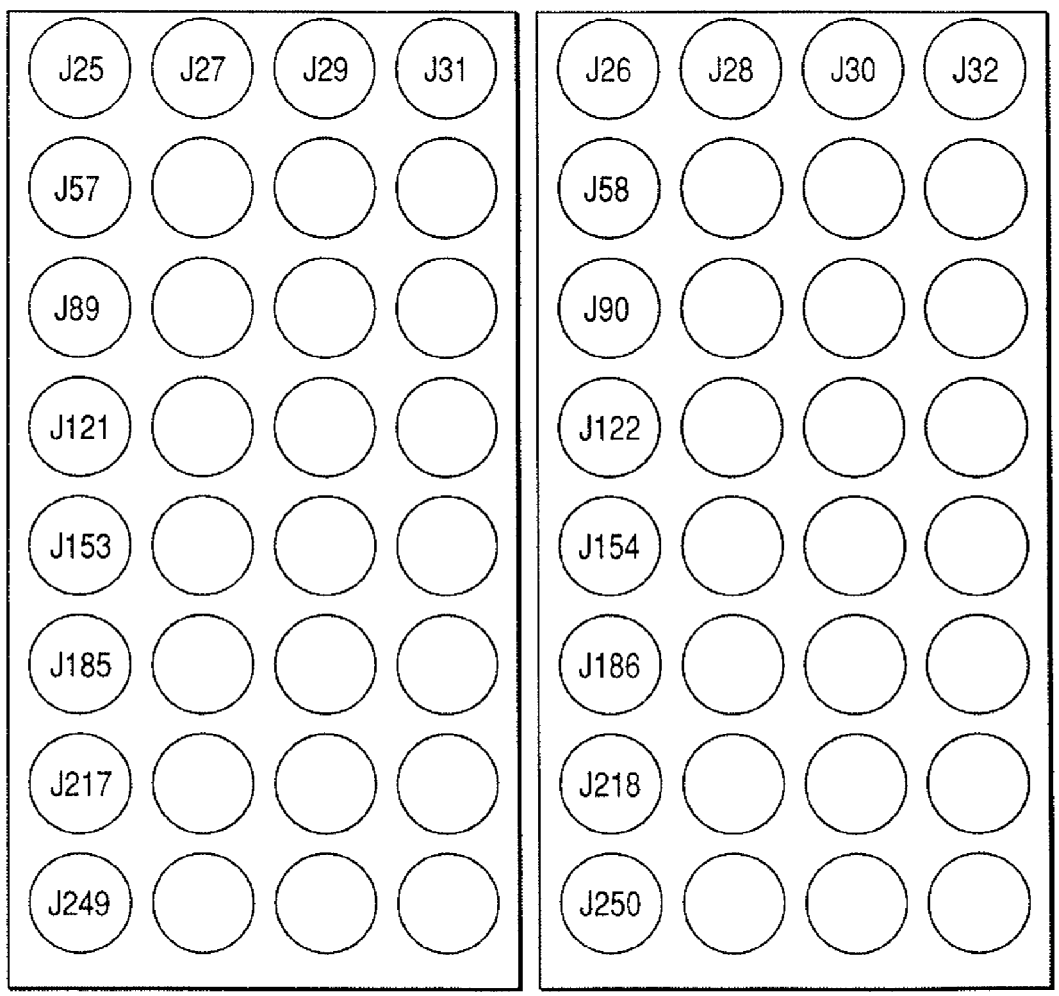
FIG. 12 is a schematic illustration of the correspondence of the addresses that are used as positional information of the liquid receiving containers 11 of the liquid ejection section 1 and the wells of each of the well plates (as continued from FIG. 11)

As shown in FIG. 4, numbers (addresses) are allocated to the liquid receiving containers 11.

As shown in FIG. 5, information indicating that the liquid receiving containers 11 belong to the liquid receiving side of the liquid applicator is stored in the information recording body 13. As a matter of course, when the liquid ejection section 1 is expanded to have 32 rows and 32 columns, both the number of rows and that of columns are equal to 32.

In each of the well plates, wells are arranged in 4 rows and 8 columns at a pitch twice as high as the pitch of arrangement of liquid receiving containers 11 in order to establish a relationship that is convenient for grouping the liquid receiving containers 11 for the purpose of increasing the capacity of the wells. The well plates can be placed at positions <1> through <8> in the well plate depot 23 that are allocated to them. Information recording bodies 31 through 38 are attached to the respective well plates.

As shown in FIG. 6, each of the information recording bodies 31 through 38 stores information indicating that the well plate belongs to the liquid receiving side of the liquid applicator, ID number, the time limit of use, the authorized maximum number of times of liquid supply, the region in the liquid supplying containers 11 to which liquid is supplied and other information.

Syringes are arranged in 4 rows and 8 columns at a pitch twice as large as the pitch of arrangement of the liquid receiving containers 11 in the syringe section 21 of the liquid supply section 2. The syringes can be driven to suck or eject respectively and simultaneously various different types of liquid by a syringe driving pump.

To read the information stored in the information recording bodies 31 through 38 of the well plates located in the well plate depot 23, the CPU section 101 firstly drives the syringe section 21 of the liquid supply section 2 to move to position <1> of the well plate depot 23 and subsequently operates the information reading device 6 to read the information stored in the information recording body 31. The CPU section 101 firstly finds out the time limit of use of the well plate there from the acquired information. If the time limit has passed, it suspends the entire operation of the liquid applicator. If the time limit has not passed yet, the CPU section 101 compares the ID number of the well plate and the ID numbers stored in the well plate information storage section (1) 7 and determines if the ID number of the well plate has been registered or not. If the ID number of the well plate has not been registered, the CPU section 101 registers the ID number in the well plate information storage section (1) 7. If, on the other hand, the ID number of the well plate has already been registered, the CPU section 101 determines if the number of times of liquid supply in the past as stored in the well plate information storage section (1) 7 has reached the authorized maximum number of times of liquid supply or not. If it is determined that the number of times of liquid supply in the past has reached the authorized maximum number of times, the CPU section 101 suspends the entire operation of the operation of the liquid applicator. If it is determined that the well plate is authorized to supply more liquid, the CPU section 101 determines the destination of supply of liquid from the well plate located at position <1> of the well plate depot 23 and stores the destination information in a predetermined storage area of the well plate information storage section (2) 8. Likewise, the CPU section 101 stores the pieces of information in the well plate information recording bodies 32 through 38 in respective program storage areas of the well plate information storage section (2) 8. FIG. 8 schematically illustrates the information stored in the well plate information storage section (2) 8.

FIGS. 9 through 12 illustrate the positional correspondence between the wells of the well plates and the region numbers of the liquid receiving containers 11.

Firstly the syringe section 21 is moved to the location in the well plate depot 23 where the well plate that corresponds to region 1 of the liquid receiving containers 11 is located and the syringe pump is driven to suck up liquid from the well plate there. Then, the syringe section 21 is moved to the crossing of the guide rail of the liquid supply section and that of the liquid ejection section 1, or region 1 of the liquid receiving containers 11, and subsequently the syringe pump is driven to eject the liquid it has sucked up into the liquid receiving containers 11 so as to supply the latter with liquid. In this way, liquid is supplied sequentially from the well plates located respectively at positions corresponding to regions 2 through 8 of the liquid receiving containers 11 to the regions 2 through 8 of the liquid receiving containers 11.

Figure 13:
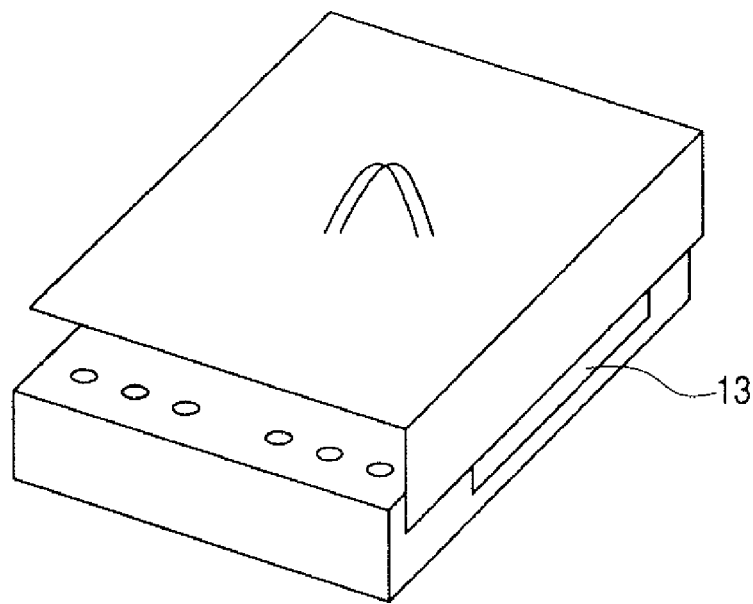
FIG. 13 is a schematic illustration of the one of the liquid receiving containers in a covered state.
Figure 14:
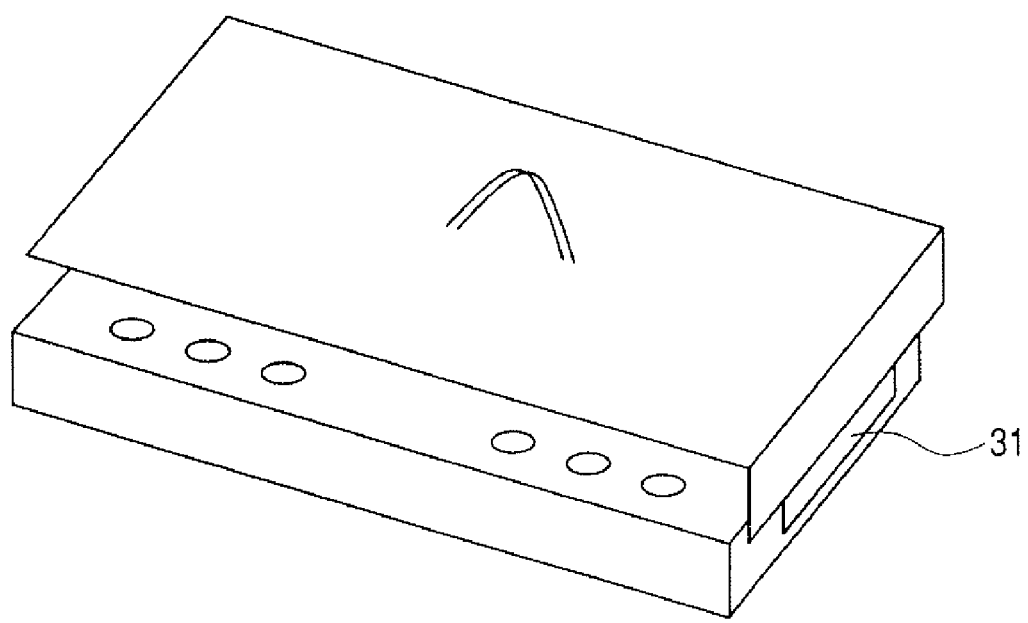
FIG. 14 is a schematic illustration of one of the well plates in a covered state.

FIG. 13 shows the cover of a liquid receiving container and FIG. 14 shows the cover of a well plate. If the liquid receiving containers and the well plates are covered by a cover during an information reading operation of the information reading device, the latter cannot read any information so that the entire operation of the liquid applicator will be suspended.

Now, the sequence of operation of the liquid applicator will be described by referring to the flow charts of FIGS. 15 through 22.

Figure 15:
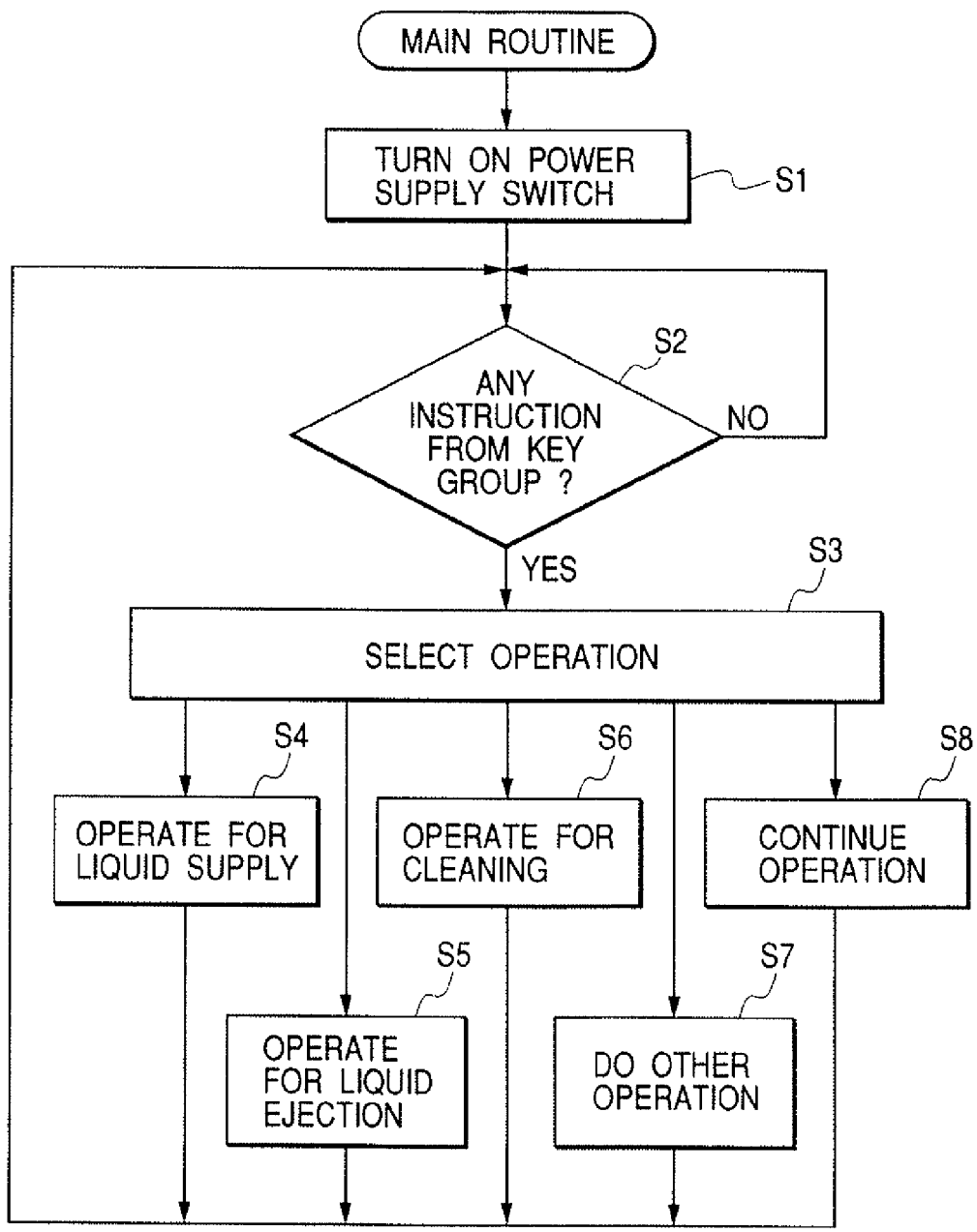
FIG. 15 is a flow chart of the main operation of the liquid applicator.
Figure 16B:
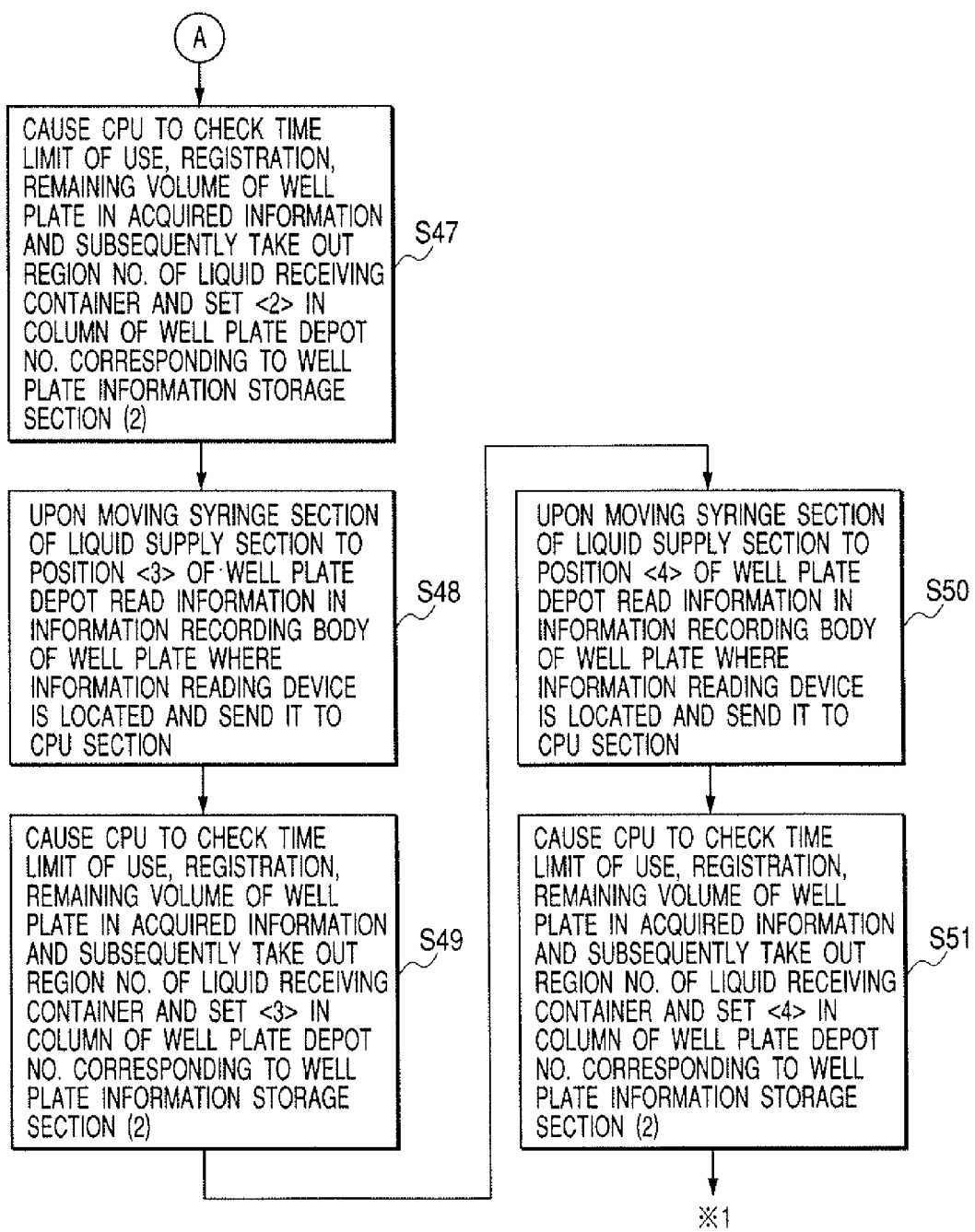
FIG. 16 is comprised of FIG. 16A and FIG. 16B showing a flow chart of the sequence of liquid supplying operation of the liquid applicator.
Figure 17B:
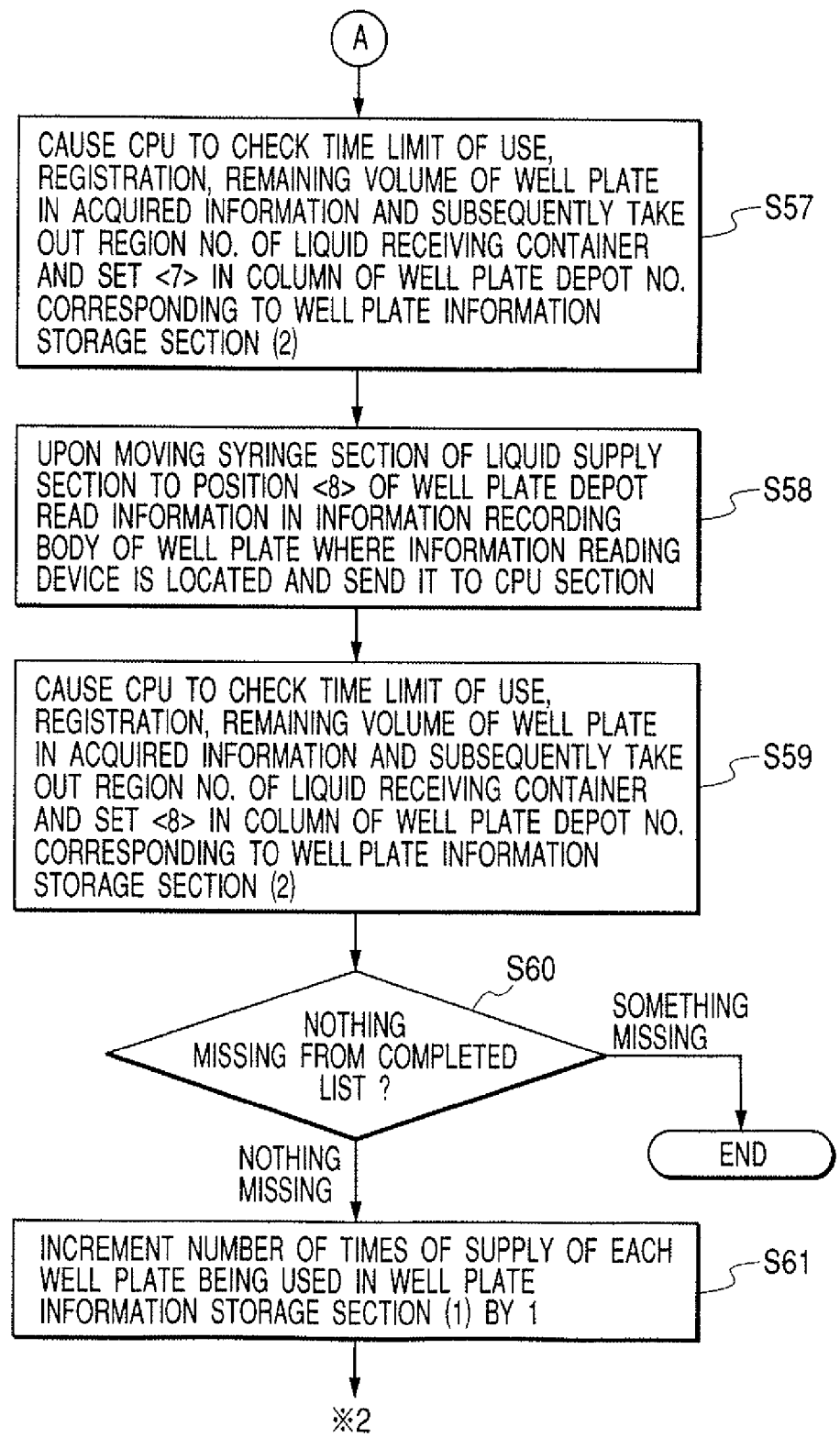
FIG. 17 is comprised of FIG. 17A and FIG. 17B showing a flow chart of the sequence of liquid supplying operation of the liquid applicator (as continued from FIGS. 16A and 16B)
Figure 18:
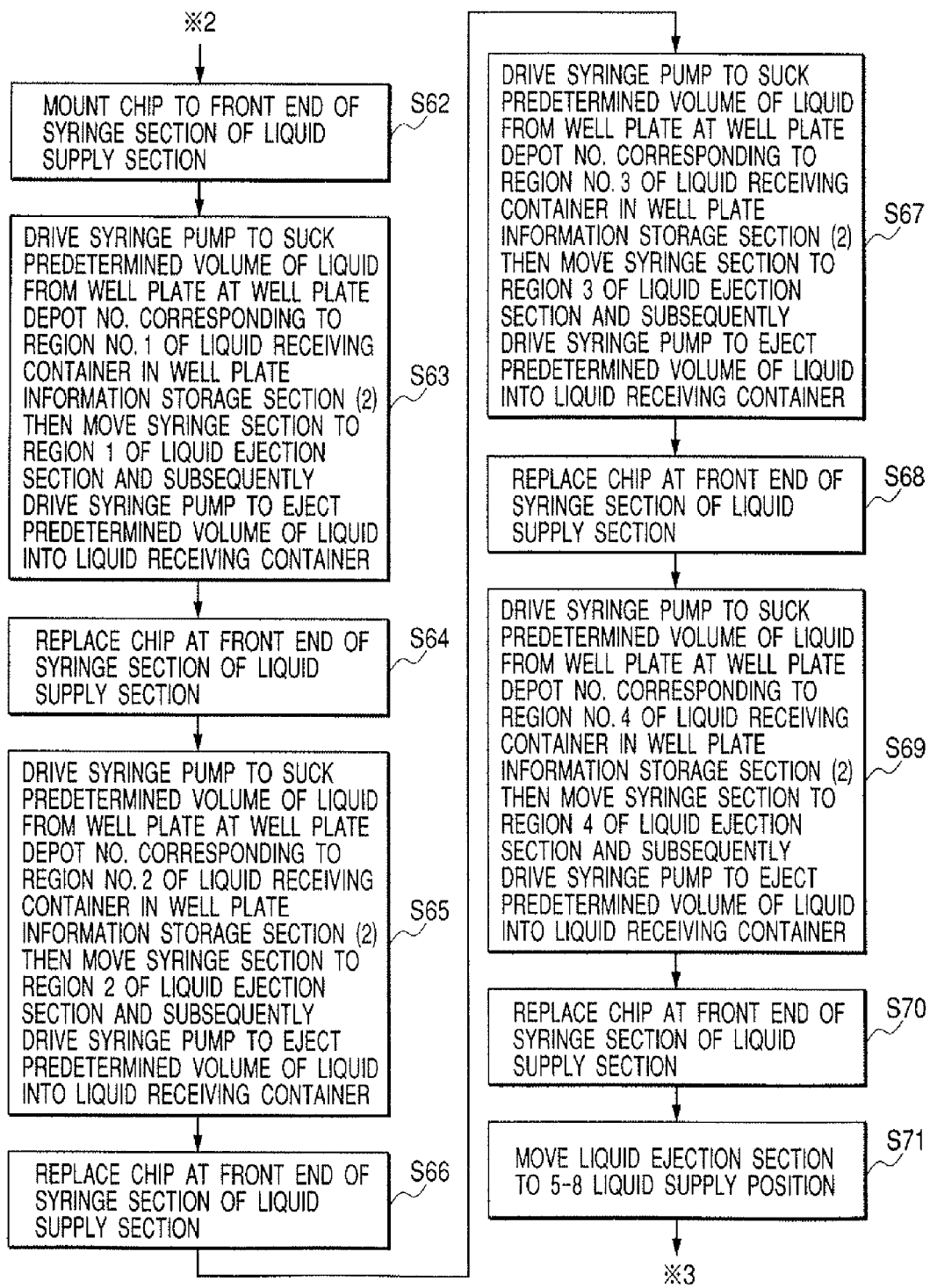
FIG. 18 is a flow chart of the sequence of liquid supplying operation of the liquid applicator (as continued from FIGS. 17A and 17B)
Figure 19:
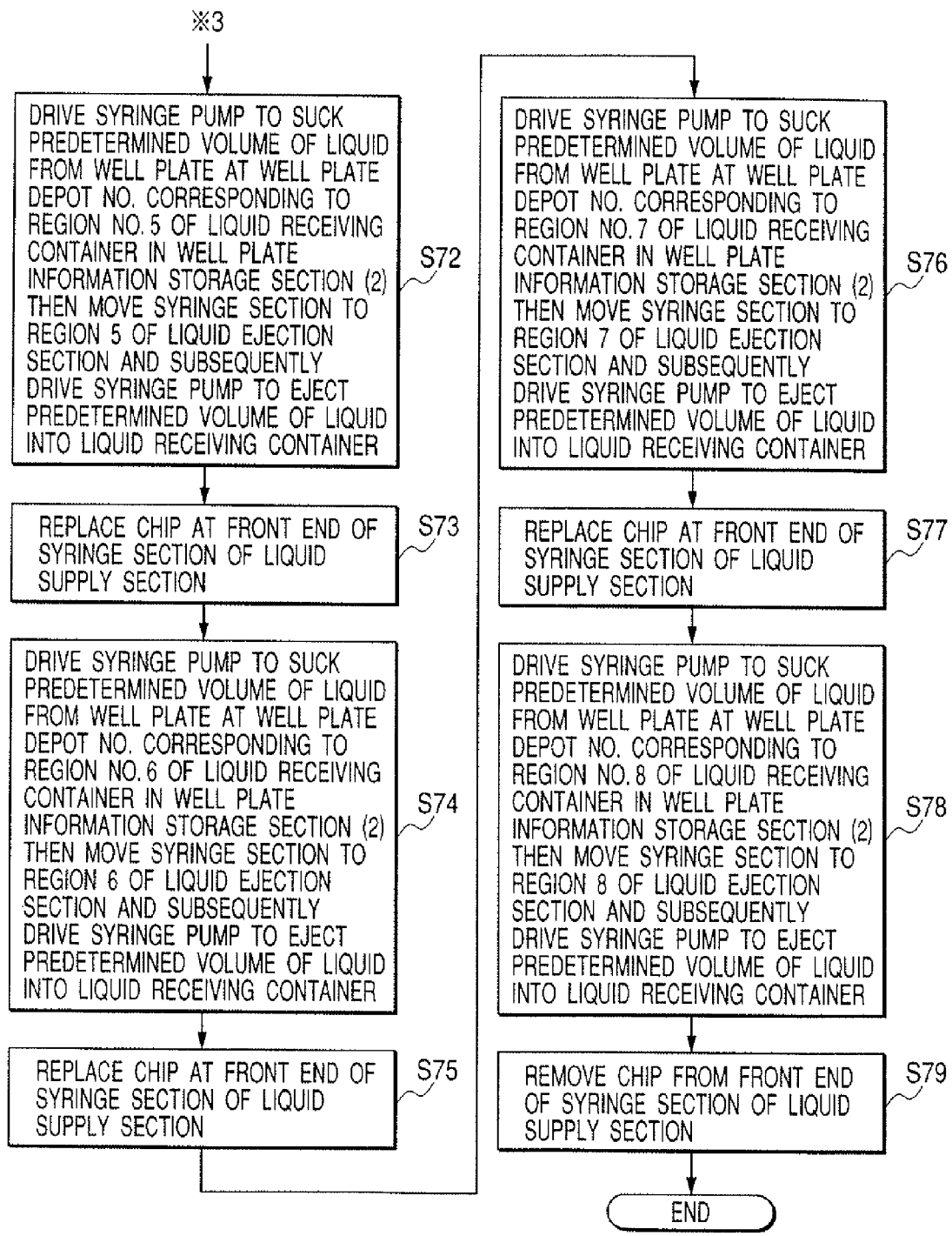
FIG. 19 is a flow chart of the sequence of liquid supplying operation of the liquid applicator (as continued from FIG. 18)

Firstly the sequence of the main operation of the liquid applicator will be described. Referring to FIG. 15, as power is supplied to the liquid applicator in Step S1, all the component sections of the liquid applicator is made ready to operate. All the component sections are initialized by the CPU section 101. Then, in Step S2, it is determined if there is any instruction from the key group or not. If there is not any instruction, it is determined again if there is any instruction or not. If there is an instruction, the CPU section 101 proceeds to Step S3, where it determines the type of the received instruction and moves to the next step in order to operate in response to the instruction. Then, the CPU section 101 proceeds sequentially to Step S4 where it operates to supply liquid, Step S5 where it operates to eject liquid, Step S6 where it operates for cleaning, Step S7 where it does some other operation and Step S8 where it operates for a continuous operation. After completing the above operations, the CPU section 101 returns to Step S2 and waits for the next instruction.

FIGS. 16A, 16B, 17A, 17B and FIGS. 18 through 19 are flow charts illustrating the liquid supplying operation of Step S4 in greater detail. Firstly, in Step S40, the CPU section 101 determines if the value stored in the liquid volume storage section 1a is equal to 0 or not. If it is not equal to 0, the CPU section 101 terminates the operation. If, on the other hand, it is equal to 0, the CPU section 101 proceeds to Step S41.

In Step S41, the CPU section 101 issues an instruction for moving the liquid ejection section 1 to the regions 1 through 4 of the liquid supply position.

The liquid ejection section 1 moves accordingly. After the completion of the movement, the CPU section 101 proceeds to Step S42.

In Step S42, the CPU section 101 issues an instruction to the liquid supply section 2 (information reading device 6) to make the latter read the information stored in the information recording body 13 of the liquid ejection section 1. In response to the issuance of the instruction, the syringe section 21 of the liquid supply section 2 moves to the liquid supply position and the information reading device 6 reads the information stored in the information recording body 13 and transmits it to the CPU section 101. When the transmission is completed, the CPU section 101 proceeds to Step S43.

In Step S43, the CPU section 101 checks the transmitted information to determine if the liquid ejection section 1 has 16 rows and 16 columns for receiving liquid or not. If it is determined that the liquid ejection section 1 has 16 rows and 16 columns for receiving liquid, the CPU section 101 proceeds to Step S44. If, on the other hand, the answer to the question is NO, the CPU section 101 terminates the current operation. If the liquid ejection section 1 is covered and hence no information can be read, it suspends the operation and tries to read the information once again after removing the cover.

Then, in Step S44, the CPU section 101 issues an instruction to the liquid supply section 2 to read the information in the information recording body 31 of the well plate located at position <1> of the well plate depot 23. In response to the instruction, the syringe section 21 of the liquid supply section 2 moves to position <1> of the well plate depot 23 and reads the information stored in the information recording body 31, which information is then sent to the CPU section 101. When the transmission is completed, the CPU section 101 proceeds to Step S45. In Step S45, the CPU section 101 checks the transmitted information for the time limit of use. If the time limit for use has passed, the CPU section 101 suspends the current operation. If, on the other hand, the time limit for use has not passed yet, the CPU section 101 proceeds with the current operation to see if the ID number of the well plate agrees with one of the ID numbers registered in the well plate information storage section (1) 7 or not. If it determines that the ID number of the well plate does not agree with any of the registered ID numbers, the CPU section 101 registers the ID number of the well plate. If, on the other hand, it is found that the ID number of the well plate has already been registered, the CPU section 101 compares the number of times of past liquid supply and the authorized maximum number of times of liquid supply to see if liquid can be supplied from the well plate. If it is found that liquid is not allowed to be supplied from the well plate, the CPU section 101 suspends the current operation. If, on the other hand, it is found that liquid can be supplied from the well plate, the CPU section 101 proceeds with the current operation to take out the region No. of the liquid receiving containers that is the destination of liquid supply and sets <1> in the column for the well plate depot position No. that corresponds to the region No. of the liquid receiving containers in the well plate information storage section (2) 8.

If the current operation is suspended and the well plate in question is subsequently replaced, then the CPU section 101 resumes the current operation to try to read the information once again. If no well plate is placed in position or covered, it suspends the operation. After placing a well plate or removing the cover, the CPU section 101 tries to read the information once again.

The CPU section 101 follows a similar procedure from Step S46 to Step S59 and all the data necessary for supplying liquid are stored in the well plate information storage section (2) 8. Then, the CPU section 101 proceeds to Step S60.

In Step S60, the CPU section 101 checks the information stored in the well plate information storage section (2) 8. More specifically, it checks if the well plate information storage section (2) 8 stores all the different position numbers that correspond to the regions No. 1 through 8 of the liquid receiving containers or not. If all the different position numbers are stored, the CPU section 101 proceeds to Step S61.

If, on the other hand, the well plate information storage section (2) 8 does not store all the different position numbers, the CPU section 101 terminates the current operation.

In Step S61, the CPU section 101 increments the number of times of liquid supply of each well plate to be used as stored in the well plate information storage section (1) 7 by +1 for updating. Then, it proceeds to Step S62.

In Step S62, the CPU section 101 issues an instruction to the liquid supply section 2 so as to cause the latter to replace the tips at the front ends of the syringes. In response to the instruction, the syringe section 21 of the liquid supply section 2 moves to the tip replacing section 22 and replaces the tips at the front ends of the syringes. After the completion of the tip attaching operation, the CPU section 101 proceeds to Step S63.

In Step S63, the CPU section 101 reads the position No. of the well plate depot that corresponds to the region No. 1 of the liquid receiving containers 11 from the well plate information storage section (2) 8. Then, it issues an instruction to the liquid supply section 2 so as to cause the latter to supply liquid from the well plate located at the read out position No. of the well plate depot 23 to the region 1 of the liquid receiving containers 11. In response to the instruction, the liquid supply section 2 moves the syringe section 21 to the position with the read out position No. of the well plate depot 23 and subsequently operates for sucking liquid. Then, the liquid supply section 2 moves the syringe section 21 to the region 1 of the liquid receiving containers 11 and causes the latter to eject the sucked liquid into the liquid receiving containers 11. After the completion of the sucking operation, the CPU section 101 proceeds to Step S64.

In Step S64, the CPU section 101 issues an instruction to the liquid supply section 2 to cause the latter to replace the tips. In response to the instruction, the liquid supply section 2 moves the syringe section 21 to the tip replacing section 22 and replaces the tips.

The CPU section 101 follows a similar procedure from Step S65 to Step S69 so that liquid is supplied to the regions 2 through 4 of the liquid receiving containers 11.

The tips are replaced in Step S70 and then the CPU section 101 proceeds to Step S71, where it issues an instruction for moving the liquid ejection section 1 to the regions 5 through 8 of the liquid supply position. The liquid ejection section 1 moves accordingly. After the completion of the movement, the CPU section 101 proceeds to Step S72.

The CPU section 101 follows a similar procedure from Step 72 to Step 79 and liquid is supplied to the regions 5 through 8 of the liquid receiving containers 11 to complete the entire sequence of liquid supplying operation.

Figure 20:
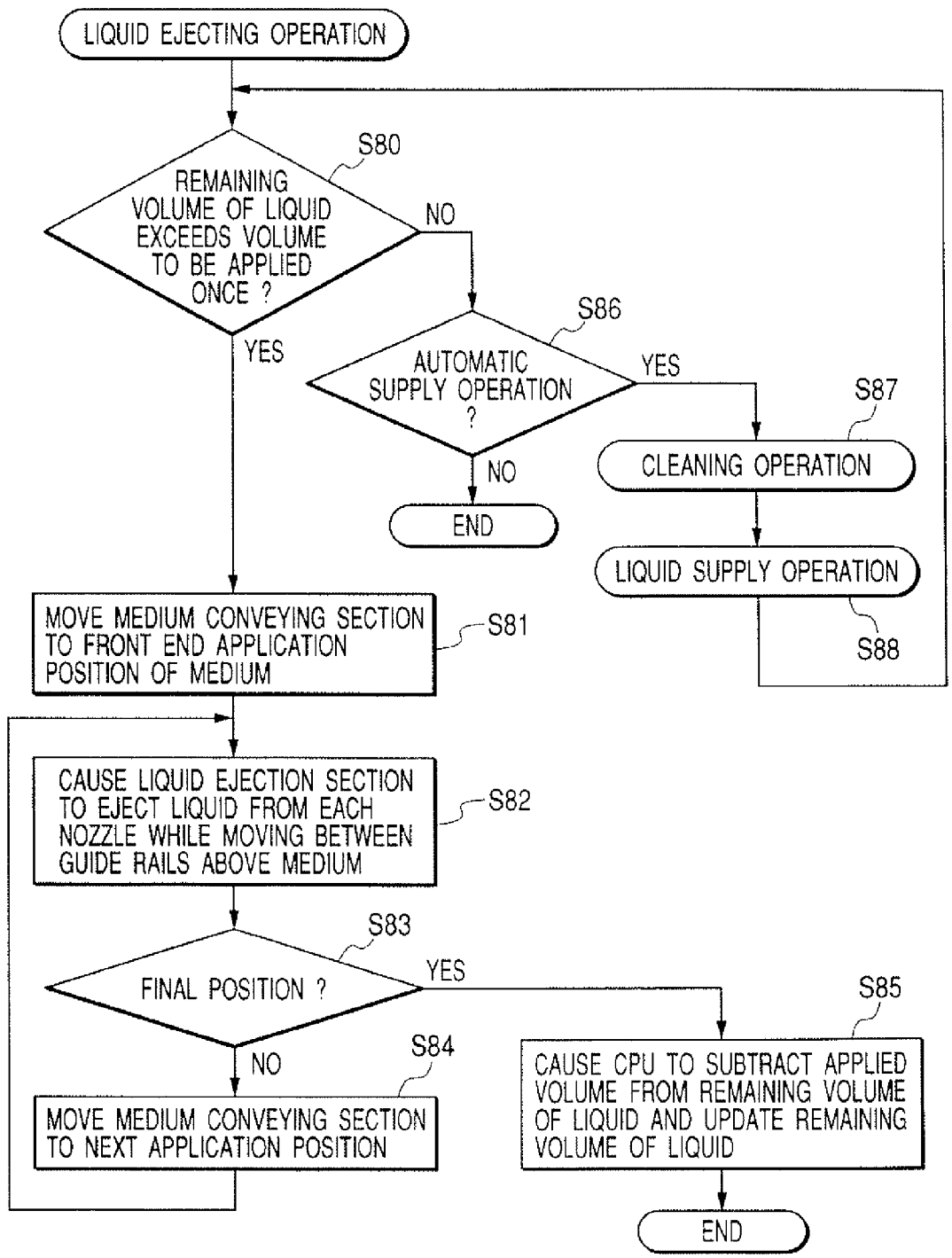
FIG. 20 is a flow chart of the sequence of liquid ejecting operation of the liquid applicator.

FIG. 20 is a flow chart of the sequence of liquid ejecting operation of the liquid applicator.

Firstly, in Step S80, the CPU section 101 determines if the value of the volume of liquid stored in the liquid volume storage section 1a is greater than the lower limit value that ensures a reliable liquid applying operation plus the largest amount of liquid that can be consumed in a single liquid applying operation or not.

The CPU section 101 proceeds to Step S81 when the value of the volume of stored liquid is greater, whereas the CPU section 101 moves to Step S86 when the value is smaller.

In Step S81, the CPU section 101 issues an instruction to the medium conveying section 4 to move to the front end position of the medium where a liquid applying operation starts. In response to the instruction, the medium conveying section 4 moves to the front end position of the medium where a liquid applying operation starts. When the medium conveying section 4 has moved to that position, the CPU section 101 proceeds to Step S82.

In Step S82, the CPU section 101 issues an instruction to the liquid ejection section 1 to cause the latter to operate the nozzles and perform a liquid applying operation, while moving along the guide rail located above the medium. In response to the instruction, the liquid ejection section 1 performs a liquid applying operation, while moving along the guide rail located above the medium. After the completion of the operation, the CPU section 101 proceeds to Step S83.

In Step S83, the CPU section 101 determines if liquid has been applied to the entire surface of the medium or not. It proceeds to Step S84 when the answer to the question is NO, whereas it proceeds to Step S85 when the answer is YES.

In Step S84, the CPU section 101 issues an instruction to move the medium conveying section 4 to the next liquid applying position. In response to the instruction, the medium conveying section 4 moves the medium to the next liquid applying position. Then, the CPU section 101 returns to Step S82.

In Step S85, the CPU section subtracts the value of the volume of the applied liquid from the value read out from the liquid volume storage section 1a and writes the result in the liquid volume storage section 1a.

Thus, the sequence of liquid ejecting operation ends.

In Step S86, the CPU section 101 determines if the scheme of automatically supplying liquid when the liquid storage is insufficient is operating properly or not. If the answer to the question is NO, it terminates the current operation.

If, on the other hand, the answer to the question is YES, it proceeds to Step S87.

In Step S87, the CPU section 101 performs a cleaning operation, which will be described hereinafter. After the completion of the cleaning operation, it proceeds to Step S88.

In Step S88, the CPU section 101 performs a liquid supplying operation, which is described above.

After the completion of the liquid supplying operation, the CPU section 101 proceeds to Step S80.

Figure 21:
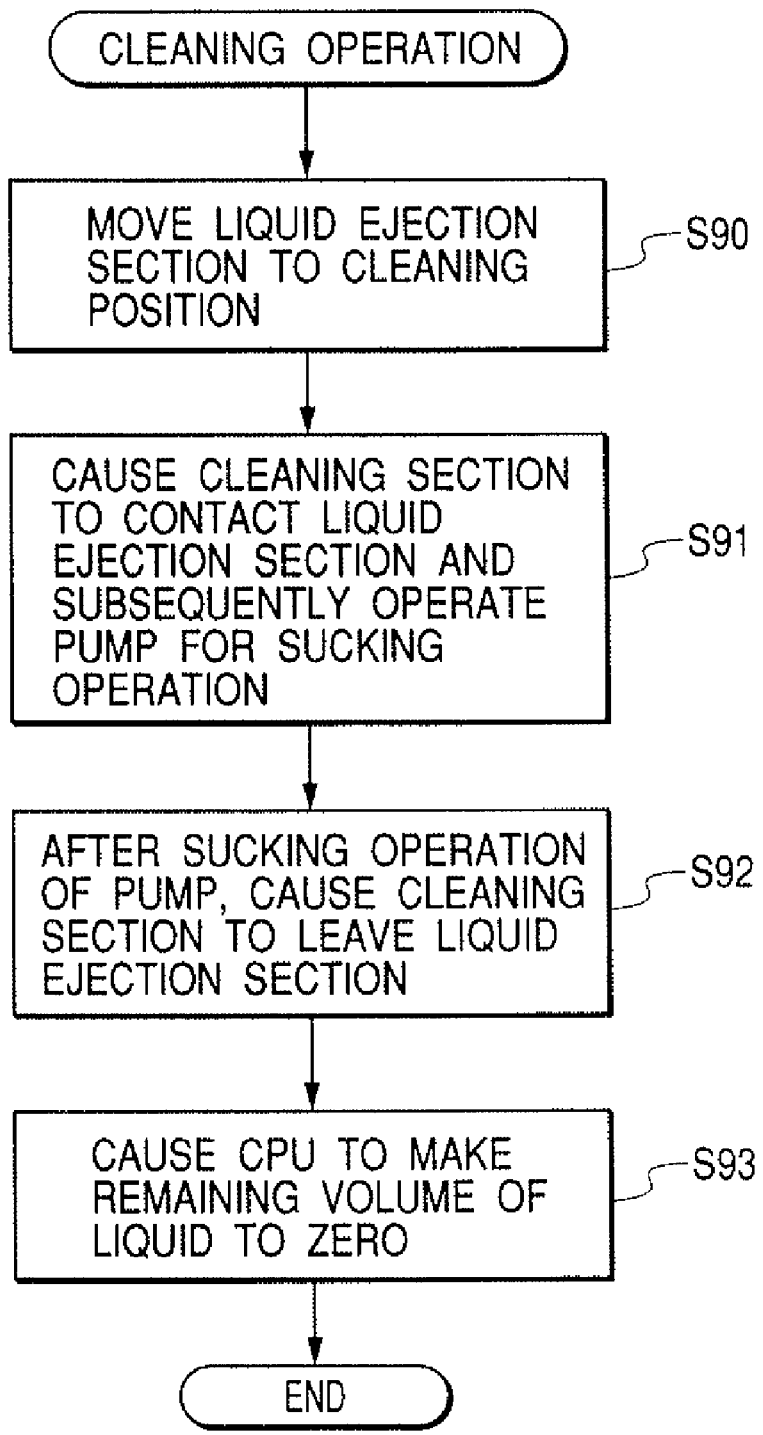
FIG. 21 is a flow chart of the sequence of cleaning operation of the liquid applicator.

FIG. 21 is a flow chart of the sequence of cleaning operation of the liquid applicator, illustrating it in detail. Firstly, in Step S90, the CPU section 101 issues an instruction to the liquid ejection section 1 to move to the cleaning section 3. In response to the instruction, the liquid ejection section moves to the cleaning section 3. After the completion of the movement, the CPU section 101 proceeds to Step S91.

In Step S91, the CPU section 101 issues an instruction to perform a cleaning operation. Accordingly, the cleaning section 3 starts a cleaning operation. At this time, the cleaning section 3 raises itself until it comes to contact the lower surface of the liquid ejection section 1. Once the cleaning section 3 contacts the lower surface of the liquid ejection section 1, it starts to drive the pump it contains in the inside to suck out the liquid remaining in the liquid ejection section 1. When the liquid is thoroughly sucked out, the CPU section 101 proceeds to Step S92, where the cleaning section 3 moves down to the original position and terminates its cleaning operation.

After the completion of the downward movement of the cleaning section 3, the CPU section 101 proceeds to Step S93 to terminate the entire operation.

In Step S93, the CPU section 101 writes 0 in the liquid volume storage section 1a.

Thus, the entire cleaning operation ends.

Figure 22:
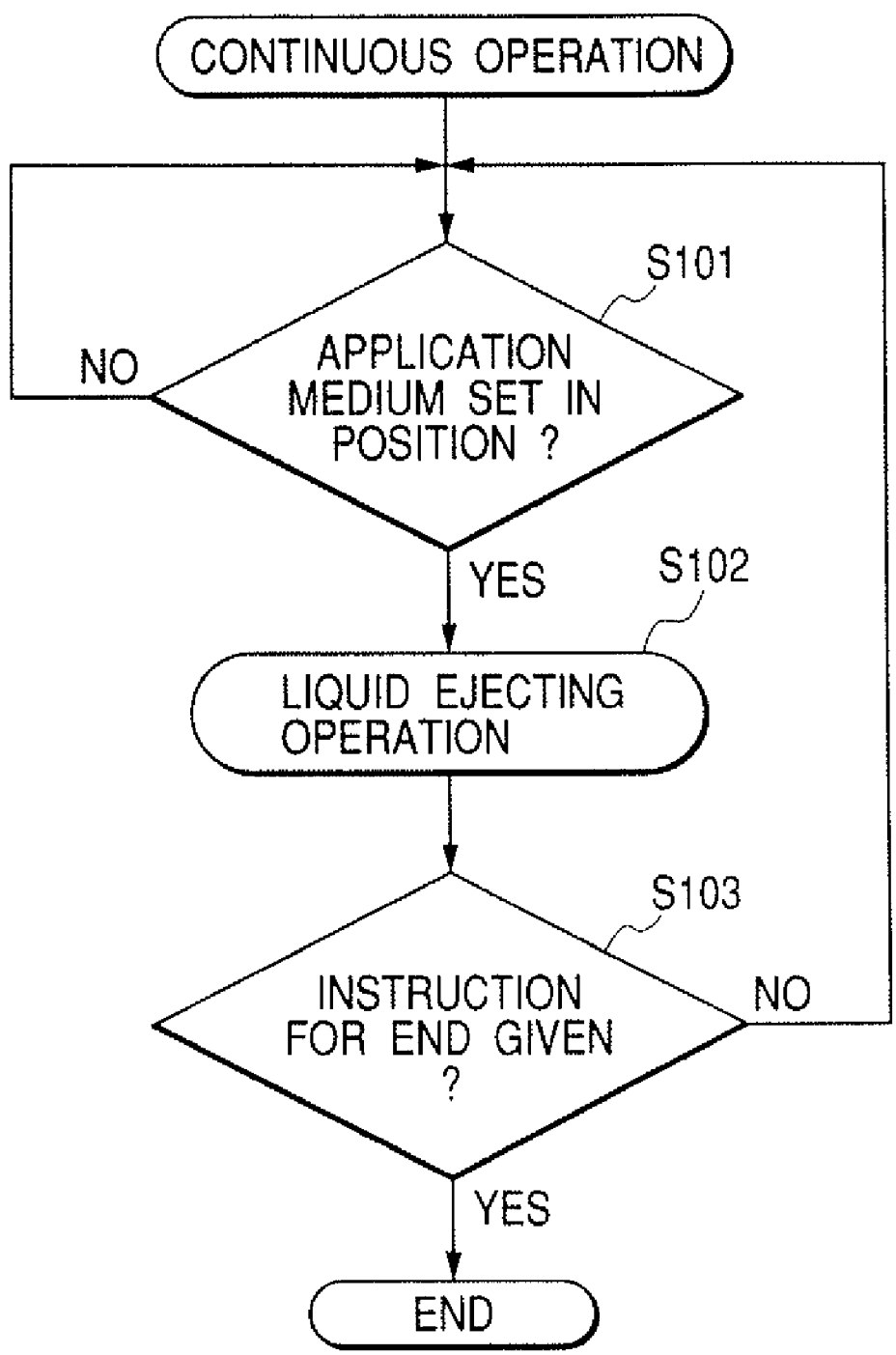
FIG. 22 is a flow chart of the sequence of continuous operation of the liquid applicator.

FIG. 22 is a detailed flow chart of the sequence of continuous operation of the liquid applicator. Firstly, in Step S10, the CPU section 101 determines if a medium is set in position in the medium conveying section 4 or not. When the answer to this question is NO, it stands by in this step. Once it is confirmed that a medium is set in position, then the CPU section 101 proceeds to Step S102.

In Step S102, the CPU section 101 starts a liquid ejecting operation. After the completion of the liquid ejecting operation, the CPU section 101 proceeds to Step S103.

In Step S103, the CPU section 101 determines if there is an instruction for completing a continuous operation or not. If there is no such an instruction, it proceeds to Step S101.

If, on the other hand, there is a command for completing a continuous operation, it completes a continuous operation.

Another Embodiment

This embodiment realizes a part of the above-described embodiment in a different manner. The part is the syringe section of the liquid supply section. More specifically, the syringe section is not of a tip replacement type but of a type that the syringes directly hold liquid. Thus, this embodiment is realized by replacing the tip replacing section with a syringe cleaning section.

While this embodiment operates like the above embodiment for sucking and ejecting liquid, a tip replacing operation is replaced by a syringe cleaning operation in this embodiment.

Cleaning solution is supplied to the syringe cleaning section and the syringes suck and eject cleaning solution for a cleaning operation.

While bar codes are used for transmitting information, other means may alternatively be used. For example, a combination of wireless tags and a wireless tag reading device or a combination of magnetic seals and a magnetic reading device may be used.

Others

While the present invention relates to a liquid applicator of the ink-jet ejection type, the features of the present invention are particularly effective when the liquid applicator comprises an ejection head that is provided with a means for generating thermal energy to be used for ejecting liquid (e.g., electrothermal transducer, a laser, etc.) so that the state of liquid may be changed by generated thermal energy. Then, liquid can be applied highly densely and precisely.

The configuration and the underlying principle of such a liquid applicator preferably conform to those disclosed in U.S. Pat. Nos. 4,723,129 and 4,740,796. The disclosed principle can also be applied to a liquid applicator of the so-called on-demand type or the continuous type. Particularly, an on-demand type liquid applicator will be advantageous because the electrothermal transducer that is arranged to correspond to a liquid-holding sheet or a liquid path is caused to generate thermal energy by applying a drive signal for causing a rapid temperature rise surpassing nucleate boiling in response to application information and produce film boiling on the heat acting surface of the application head so as to consequently form a bubble in liquid that shows one-to-one correspondence to the drive signal. Liquid is ejected by way of an ejection opening as a result of growth and contraction of the bubble to form at least a drop. The drive signal is preferably a pulse signal because the bubble can grow and contract immediately and appropriately so that liquid can be ejected highly responsively when the drive signal is a pulse signal. A pulse-shaped drive signal as described in U.S. Pat. No. 4,463,359 or U.S. Pat. No. 4,345,262 may preferably be used for the purpose of the present invention.

A liquid applying operation using a liquid applicator according to the invention can be performed highly satisfactorily when the requirements for the temperature rising rate of a heat acting surface as described in U.S. Pat. No. 4,313,124 are met.

The application head may be configured by combining ejection ports, liquid paths and electrothermal transducers (linear liquid flow paths or rectangular liquid flow paths) as disclosed in the related ones of the above listed patent documents. Additionally, a configuration disclosed in U.S. Pat. No. 4,558,333 that describes an arrangement of a thermal acting section in a curved region and one disclosed in U.S. Pat. No. 4,459,600 are also found within the scope of the present invention. Furthermore, a configuration employing a slit that is commonly used as ejection section for a plurality of electrothermal transducers as disclosed in Japanese Patent Application Laid-Open No. S59-123670 and one arranging an opening for absorbing pressure waves of thermal energy so as to correspond to an ejecting section as disclosed in Japanese Patent Application Laid-Open No. S59-138461 may effectively be used for the purpose of the present invention. In short, according to the invention, liquid can be precisely and efficiently applied regardless of the configuration of the application head.

Preferably, an ejection recovery means of the application head and/or a provisional auxiliary means may be added to a liquid applicator according to the invention to reliably ensure the advantages of the present invention. Specific examples of such means that can be used for the application head include a capping means, a cleaning means, a pressurizing or suction means, an electrothermal transducers, a provisional heating means realized by combining such electrothermal transducers or different heating elements and a provisional ejection means for ejecting liquid but not for applying liquid.

What is claimed is:

1. A method of applying plural types of liquid onto a medium, comprising:
    a supply step for preparing a liquid ejection section having plural sets each comprising a liquid ejecting nozzle for ejecting liquid, a liquid containing section communicating with the liquid ejecting nozzle and a supply port for supplying liquid to the liquid containing section, the plural sets being capable of ejecting different types of liquid from each other, and wherein the supply step further comprises supplying the plural types of liquid to the corresponding supply ports; and
    an application step for ejecting the plural types of liquid from the liquid ejecting nozzles,
    wherein the supply ports are openings arranged in an array on a top surface of the liquid ejection section,
    wherein the method includes preparing a liquid supply section having plural syringes arranged as corresponding to the array of the supply ports, wherein each of the plural syringes has a function for performing suction and ejection of liquid, and
    wherein the supply step includes opposing the top surface having the supply ports and the plural syringes to each other to thereby supply the plural types of liquid respectively from the plural syringes.

2. A method of manufacturing a probe array by the method according to claim 1, wherein the plural types of liquid are plural types of probe to be fixed onto a medium.

3. A method according to claim 1, wherein the supply step includes moving one of the surface having the supply ports and the plural syringes from a first position where they do not oppose each other to a second position where they do.

4. A method of applying plural types of liquid onto a medium, comprising:

a supply step for preparing a liquid ejection section having plural sets each comprising a liquid ejecting nozzle for ejecting liquid, a liquid containing section communicating with the liquid ejecting nozzle and a supply port for supplying liquid to the liquid containing section, the plural sets being capable of ejecting different types of liquid from each other, and wherein the supply step further comprises supplying the plural types of liquid to the corresponding supply ports; and an application step for ejecting the plural types of liquid from the liquid ejecting nozzles, and a sucking step for preparing a well plate corresponding to the array of the plural syringes and sucking different types of liquid at a time from the well plate to the syringes, wherein the supply ports are arranged in an array on a surface of the liquid ejection section, wherein the method includes preparing a liquid supply section having plural syringes arranged as corresponding to the array of the supply ports, and wherein the supply step includes opposing the surface having the supply ports and the plural syringes to each other to thereby supply the plural types of liquid respectively from the plural syringes.

5. A method according to claim 4, wherein the sucking step and the supply step are repeated until a necessary amount of liquid of a necessary type is supplied to the liquid ejection section.

6. A method according to claim 4, wherein the supply ports, the syringes and wells of the well plate are arranged at intervals equal to each other.

* * * * *